United States Patent [19]

Toan

[11] Patent Number: 5,489,503
[45] Date of Patent: Feb. 6, 1996

[54] UV ABSORBERS

[75] Inventor: Vien V. Toan, Lentigny, Switzerland

[73] Assignee: Ciba-Geigy Corp., Tarrytown, N.Y.

[21] Appl. No.: 350,300

[22] Filed: Dec. 6, 1994

Related U.S. Application Data

[63] Continuation-in-part of Ser. No. 159,400, Nov. 30, 1993, abandoned.

[30] Foreign Application Priority Data

Dec. 3, 1992 [CH] Switzerland ............... 3717/92

[51] Int. Cl.$^6$ .................................. G03C 1/46
[52] U.S. Cl. .................. 430/507; 430/512; 544/116; 544/113; 544/216
[58] Field of Search .................. 430/512, 507; 544/116, 113, 216

[56] References Cited

U.S. PATENT DOCUMENTS

| | | | |
|---|---|---|---|
| 3,118,887 | 1/1964 | Hardy et al. | 544/116 |
| 3,244,708 | 4/1966 | Duennenberger et al. | 544/216 |
| 3,843,371 | 10/1974 | Piller et al. | 430/512 |
| 4,518,686 | 5/1985 | Sasaki et al. | 430/512 |
| 4,826,978 | 5/1989 | Migdal et al. | 544/216 |
| 4,853,471 | 8/1989 | Rody et al. | 548/261 |
| 4,921,966 | 5/1990 | Stegmann et al. | 548/260 |
| 4,973,701 | 11/1990 | Winter et al. | 548/260 |
| 4,973,702 | 11/1990 | Rody et al. | 548/261 |
| 5,096,781 | 3/1992 | Vieira et al. | 428/411.1 |
| 5,106,891 | 4/1992 | Valet | 524/91 |
| 5,300,414 | 4/1994 | Leppard et al. | 430/507 |
| 5,364,749 | 11/1994 | Leppard et al. | 430/507 |

FOREIGN PATENT DOCUMENTS

| | | | |
|---|---|---|---|
| 0434608 | 6/1991 | European Pat. Off. | 544/216 |
| 0442847 | 8/1991 | European Pat. Off. | |
| 0531258 | 3/1993 | European Pat. Off. | 430/512 |
| 0484695 | 3/1970 | Switzerland. | |
| 1061521 | 3/1967 | United Kingdom. | |

OTHER PUBLICATIONS

C.A. Registry No. 1440–02–4.
C.A. Registry No. 1908–78–7.
C.A. Registry No. 4517–07–1.
CA Registry No. 148236–67–3 (Dec. 1992).
CA Registry No. 148236–68–4 (Mar. 1993).
CA Registry No. 148236–58–2 (Mar. 1993).

*Primary Examiner*—Thomas R. Neville
*Attorney, Agent, or Firm*—Michele A. Kovaleski

[57] ABSTRACT

Novel UV absorbers of the bis- or tris-2'-hydroxyphenyltriazine type and their use in photographic materials, inks or recording materials for ink-jet printing, and surface coatings are described which conform to the formula

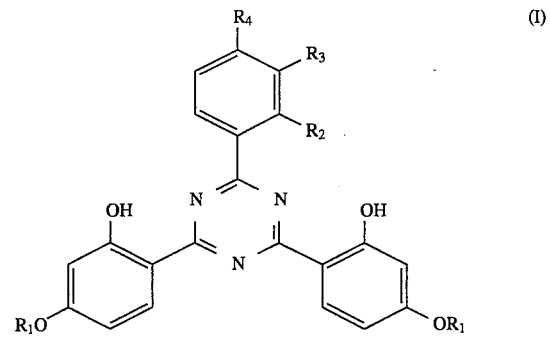

in which the radicals $R_1$ and $R_9$ are as defined in claim 1.

3 Claims, No Drawings

UV ABSORBERS

This is a continuation-in-part of application Ser. No. 08/159,400 filed Nov. 30, 1993, now Abandoned.

The invention relates to novel UV absorbers of the bis- or tris-2'hydroxyphenyltriazine type, and to the use thereof in photographic materials, inks and recording materials for ink-jet printing, and in surface coatings.

Hydroxyphenyltriazines and their use in photographic materials are known, for example, from U.S. Pat. No. 3,843,371. However, their use in photographic materials has hitherto been prevented by still not entirely satisfactory properties, for example poor chemical stability, low solubility, excessive inherent colour or inadequate absorbence.

A group of bis- and tris-2'-hydroxyphenyltriazine UV absorbers have now been found which, surprisingly, is highly satisfactory with respect to the demands made by industry. In addition, the novel compounds are dispersible in aqueous gelatine, which simplifies their incorporation into photographic coatings and makes the use of oils superfluous. The result is a low coating thickness or, for the same coating thickness, a higher concentration of UV absorbers. In particular, this group of triazines is suitable for increasing the stability of the magenta, cyan and yellow layer of photographic materials through incorporation into layers applied over the magenta or cyan layer or directly into the cyan layer.

The present invention thus relates to compounds of the formula

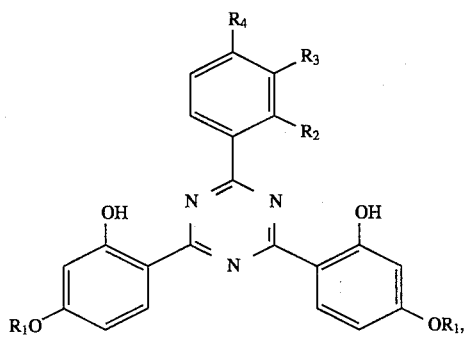

in which the radicals $R_1$, independently of one another, are —$CH_2CHR_5$—$O)_k$—$R_8$, —$CH_2$—$CH(OH)$—$CH_2$—$O$—$(CH_2CHR_5$—$O)_n$—$R_8$, —$(CH_2)_l$—$CHR_6$—$C(O)$—$O$—$(CH_2CHR_5$—$O)_n$—$R_8$ or —$CH_2$—$CH(CH_2$—$OR_7)$—$O$—$C(O)$—$(CH_2CHR_5$—$O)_n$—$R_8$;

$R_2$ is H, OH, $C_1$-$C_{12}$ alkyl, F or Cl;

$R_3$ is H, $OR_9$, $C_1$-$C_{12}$ alkyl, F or Cl;

$R_4$ is H, $OR_9$, $C_1$-$C_{12}$alkyl, F, Cl or, if $R_2$ is OH, is alternatively $OR_1$;

$R_5$ is H or $CH_3$;

$R_6$ is $C_1$-$C_{16}$alkyl or, if l is not 1, is alternatively H;

$R_7$ is $C_1$-$C_{14}$alkyl or phenyl;

$R_8$ is H, $C_1$-$C_{14}$alkyl, phenyl or ($C_1$-$C_4$alkyl)phenyl;

$R_9$ is $C_1$-$C_4$alkyl;

k is a number from 2 to 16;

l is a number from 0 to 16 and n is a number from 1 to 16.

Any $C_1$-$C_{16}$alkyl substituents in the compounds of the formula (I) are for example methyl, ethyl, propyl, butyl, pentyl, hexyl, heptyl, octyl, nonyl, decyl, undecyl, dodecyl, tetradecyl, hexadecyl or corresponding branched isomers.

Any ($C_1$-$C_4$alkyl)phenyl substituents in the compounds of the formula (I) are radicals such as tolyl or tert-butylphenyl.

$R_1$ is preferably —$CH_2$—$CH(OH)$—$CH_2$—$O$—$(CH_2CHR_5$—$O)_n$—$R_8$ or —$(CH_2)_l$—$CHR_6$—$C(O)$—$O$—$(CH_2CHR_5$—$O)_n$—$R_8$.

$R_2$, $R_3$ and $R_4$ are preferably H or one or two $C_1$-$C_4$alkyl groups.

If $R_2$ is OH, $R_4$ is preferably —$OCH_2$—$CH(OH)$—$CH_2$—$O$—$(CH_2CHR_5$—$O)_n$—$R_8$ or —$O(CH_2)_l$—$CHR_6$—$C(O)$—$O$—$(CH_2CHR_5$—$O)_n$—$R_8$.

$R_5$ or $R_6$ is preferably H.

$R_7$ or $R_8$ is preferably $C_1$-$C_8$alkyl.

k is preferably a number from 2 to 8 or 2 to 4.

l is preferably a number from 1 to 6 or 0.

n is preferably a number from 1 to 8 or 2 to 4.

Preference is given to compounds of the formula (I) in which the radicals $R_1$, independently of one another, are —$(CH_2CHR_5$—$O)_k$—$R_8$, —$CH_2$—$CH(OH)$—$CH_2$—$O$—$(CH_2CHR_5$—$O)_n$—$R_8$, —$(CH_2)_l$—$CHR_6$—$C(O)$—$O$—$(CH_2CHR_5$—$O)_n$—$R_8$ or —$CH_2$—$CH(CH_2$—$OR_7)$—$O$—$C(O)$—$(CH_2CHR_5$—$O)_n$—$R_8$;

$R_2$ is H, OH, $C_1$-$C_8$alkyl, F or Cl ;

$R_3$ is H, $OR_9$, $C_1$-$C_8$alkyl, F or Cl;

$R_4$ is H, $OR_9$, $C_1$-$C_8$alkyl, F, Cl or, if $R_2$ is OH, is alternatively $OR_1$;

$R_5$ is H;

$R_6$ is $C_1$-$C_{12}$alkyl or, if l is not 1, is alternatively H;

$R_7$ is $C_1$-$C_8$alkyl;

$R_8$ is H or $C_1$-$C_{10}$alkyl;

$R_9$ is $C_1$-$C_4$alkyl;

k is a number from 2 to 12;

l is a number from 0 to 12, and n is a number from 1 to 12.

Particular preference is given to compounds of the formula (I) in which the radicals $R_1$, independently of one another, are—$CH_2$—$CH(OH)$—$CH_2$—$O$—$(CH_2CHR_5$—$O)_n$—$R_8$ or —$(CH_2)_l$—$CHR_6$—$C(O)$—$O$—$(CH_2CHR_5$—$O)_n$—$R_8$;

$R_2$ is H, OH or $C_1$-$C_4$alkyl;

$R_3$ is H, $OR_9$ or $C_1$-$C_4$alkyl;

$R_4$ is H, $OR_9$, $C_1$-$C_4$alkyl, F, Cl or, if $R_2$ is OH, is alternatively $OR_1$;

$R_5$ is H;

$R_6$ is $C_1$-$C_6$alkyl;

$R_8$ is $C_1$-$C_4$alkyl;

$R_9$ is $C_1$-$C_4$alkyl;

l is 0, and n is a number from 1 to 12.

The present invention furthermore relates to the use of a compound of the formula (I) as a light stabilizer, in particular a UV stabilizer, in photographic materials, and to the photographic material containing a compound of the formula (I); it also being possible to use a mixture of compounds of formula (I).

The novel compounds can be used in photosensitive materials of all types. For example, they can be employed for colour paper, colour reversal paper, direct-positive colour material, colour negative film, colour positive film, colour reversal film, inter alia. They are preferably used, inter alia, for photosensitive colour material which contains a reversal substrate or forms positives.

Furthermore, the novel triazines can be combined with further UV absorbers, in particular with those which can be dispersed in aqueous gelatine.

It is also possible to use the novel triazines with other UV absorbers, such as hydroxyphenylbenzotriazoles (cf., for example, U.S. Pat. Nos. 4,853,471, 4,973,702, 4,921,966 and 4,973,701), benzophenones, oxanilides, cyanoacrylates, salicylates, acrylonitriles or thiazolines, but it is advantageous to employ these other oil-dissolved UV absorbers in different layers in the photographic material than the novel UV absorbers.

In particular, photographic materials similar to those described in U.S. Pat. No. 4,518,686 can successfully be stabilized.

The present application thus relates to photographic material comprising, on a support, a blue-sensitive, a green-sensitive and/or a red-sensitive silver-halide emulsion layer and, if desired, a protection layer, where a layer containing a UV absorber is arranged above the uppermost silver-halide emulsion layer, wherein the UV absorber conforms to the formula (I).

In a further embodiment, the novel material contains a layer containing a UV absorber of the formula (I) arranged between the green-sensitive and the red-sensitive silver-halide emulsion layers, where a further layer containing a UV absorber of the formula (I) may be arranged above the uppermost silver-halide emulsion layer.

Good results are also achieved if the UV absorber of the formula (I) is additionally present in the red-sensitive silver-halide emulsion layer.

Preference is furthermore given to photographic materials which contain a layer containing a compound of the formula (I) above the uppermost silver-halide emulsion layer and/or between the green-sensitive and the red-sensitive silver-halide emulsion layers, an oil-soluble UV absorber additionally being present in a layer containing no UV absorber of the formula (I).

It may furthermore be advantageous for all or some of said layers possibly containing a UV absorber to contain a UV absorber of the formula (I) and/or a further UV absorber which can be dispersed in aqueous gelatine, but a UV absorber of the formula (I) must be present in at least one layer.

The novel material preferably contains gelatine interlayers between the silver-halide emulsion layers.

Preference is given to photographic materials in which the silver-halide in the blue-sensitive, green-sensitive and/or red-sensitive layers is silver chloride/bromide comprising at least 90 mol % of silver chloride.

Preference is furthermore given to photographic materials in which the silver-halide emulsion layers are in the sequence blue-sensitive, green-sensitive and red-sensitive silver-halide emulsion layers.

The novel photographic materials offer the advantage over materials containing benzotriazole UV absorbers, that the UV absorbers of the formula (I) are required in a relatively small amount to ensure adequate protection against UV radiation. This means that the thickness of the layers containing the UV absorbers of the formula (I) can be very thin, which has a positive effect, for example, on the sharpness of the images produced using this material.

Typical and preferred compounds of the formula (I) are shown in the table below:

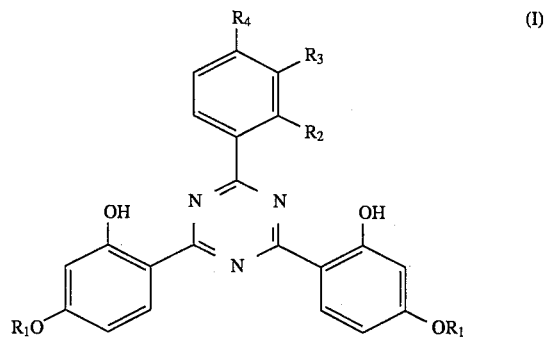

TABLE 1

| Comp. No. | $R_4, R_3, R_2$ | $R_1$ |
| --- | --- | --- |
| (1) | H, H, H | —$CH_2CH(OH)CH_2O(CH_2CH_2O)_{7/8}CH_3$ |
| (2) | H, H, H | —$CH_2CH(OH)CH_2O(CH_2CH_2O)_1C_2H_5$ |
| (3) | H, H, H | —$CH_2CH(OH)CH_2O(CH_2CH_2O)_1C_4H_9$ |
| (4) | H, H, H | —$CH_2CH(OH)CH_2O(CH_2CH_2O)_2CH_3$ |
| (5) | $CH_3$, H, H | —$CH_2CH(OH)CH_2O(CH_2CH_2O)_2CH_3$ |
| (6) | H, H, H | —$CH_2CH(OH)CH_2O(CH_2CH_2O)_2C_2H_5$ |
| (7) | H, H, H | —$CH_2CH(OH)CH_2O(CH_2CH_2O)_2CH_3/C_2H_5$ |
| (8) | H, H, H | —$CH_2CH(OH)CH_2O(CH_2CH_2O)_2C_4H_9$ |
| (9) | H, H, H | —$CH_2CH(OH)CH_2O(CH_2CH_2O)_{2/3}CH_3$ |
| (10) | H, H, H | —$CH_2CH(OH)CH_2O(CH_2CH_2O)_3CH_3$ |
| (11) | H, H, H | —$CH_2CH(OH)CH_2O(CH_2CH_2O)_3C_2H_5$ |
| (12) | H, H, H | —$CH_2CH(OH)CH_2O(CH_2CH_2O)_3C_4H_9$ |
| (13) | H, H, H | —$CH_2CH(OH)CH_2O(CH_2CH_2O)_{12/13}CH_3$ |
| (14) | H, H, H | —$CH(CH_3)C(O)O(CH_2CH_2O)_3CH_3$ |
| (15) | H, H, H | —$CH(CH_3)C(O)O(CH_2CH_2O)_3C_2H_5$ |

TABLE 1-continued

| Comp. No. | $R_4, R_3, R_2$ | $R_1$ |
| --- | --- | --- |
| (16) | H, H, H | $-CH(CH_3)C(O)O(CH_2CH_2O)_3C_6H_{13}$ |
| (17) | $OR_1$, H, OH | $-CH_2CH(OH)CH_2O(CH_2CH_2O)_{7/8}CH_3$ |
| (18) | $OR_1$, H, OH | $-CH_2CH(OH)CH_2O(CH_2CH_2O)_1C_2H_5$ |
| (19) | $OR_1$, H, OH | $-CH_2CH(OH)CH_2O(CH_2CH_2O)_1C_4H_9$ |
| (20) | $OR_1$, H, OH | $-CH_2CH(OH)CH_2O(CH_2CH_2O)_2CH_3$ |
| (21) | $OR_1$, H, OH | $-CH_2CH(OH)CH_2O(CH_2CH_2O)_2C_2H_5$ |
| (22) | $OR_1$, H, OH | $-CH_2CH(OH)CH_2O(CH_2CH_2O)_2CH_3/C_2H_5$ |
| (23) | $OR_1$, H, OH | $-CH_2CH(OH)CH_2O(CH_2CH_2O)_2C_4H_9$ |
| (24) | $OR_1$, H, OH | $-CH_2CH(OH)CH_2O(CH_2CH_2O)_{2/3}CH_3$ |
| (25) | $OR_1$, H, OH | $-CH_2CH(OH)CH_2O(CH_2CH_2O)_3CH_3$ |
| (26) | $OR_1$, H, OH | $-CH_2CH(OH)CH_2O(CH_2CH_2O)_3C_4H_9$ |
| (27) | $OR_1$, H, OH | $-CH_2CH(OH)CH_2O(CH_2CH_2O)_{12/13}CH_3$ |
| (28) | $OR_1$, H, OH | $-CH(CH_3)C(O)O(CH_2CH_2O)_2CH_3$ |
| (29) | $OR_1$, H, OH | $-CH(CH_3)C(O)O(CH_2CH_2O)_3CH_3$ |

Yellow couplers which can be used in the novel material are preferably compounds of the formula A

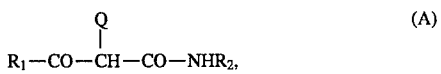

in which $R_1$ is alkyl or aryl, $R_2$ is aryl, and Q is hydrogen or a group which can be eliminated by reaction with the oxidized developer.

A group of yellow couplers comprises compounds of the formula A in which $R_1$ is t-butyl and $R_2$ is a group of the formula

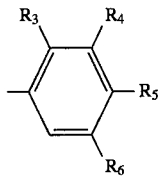

in which $R_3$ is hydrogen, halogen, alkyl or alkoxy, and $R_4$, $R_5$ and $R_6$ are hydrogen, halogen, alkyl, alkenyl, alkoxy, aryl, carboxyl, alkoxycarbonyl, carbamoyl, sulfonyl, sulfamoyl, alkylsulfonamino, acylamino, ureido or amino.

Preference is given to compounds in which $R_3$ is chlorine, $R_4$ and $R_5$ are hydrogen and $R_6$ is acylamino. These also include the compounds of the formula

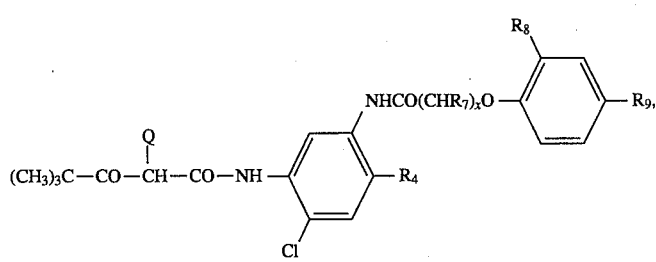

in which x is from 0 to 4, $R_7$ is hydrogen or alkyl, and $R_8$ and $R_9$ are alkyl.

Another group of yellow couplers conforms to the formula B

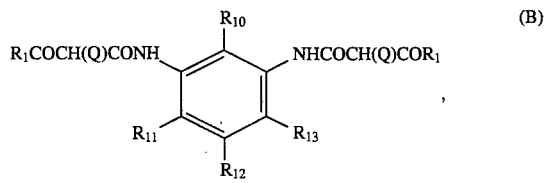

in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, carbamoyl, sulfonyl, sulfamoyl, sulfonamido, acylamino, ureido or amino, and R and Q are as defined above.

This includes compounds of the formula B in which $R_1$ is t-butyl, $R_{10}$ is chlorine, $R_{11}$ and $R_{13}$ are hydrogen, and $R_2$ is alkoxycarbonyl.

In the compounds of the formulae A and B, the leaving group Q may be hydrogen or a heterocyclic group

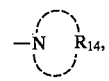

in which $R_{14}$ is a divalent organic group which supplements the ting to form a 4–7-membered ring, or Q is an $-OR_{15}$ group in which $R_{15}$ is alkyl, aryl, acyl or a heterocyclic radical.

Typical examples of customary yellow couplers are compounds of the formulae:

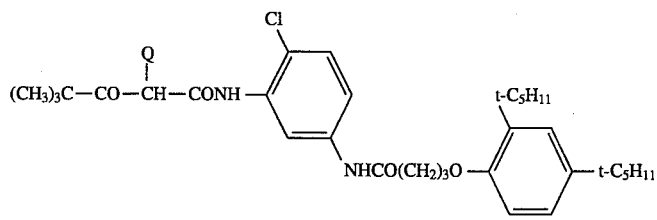
a) Q = 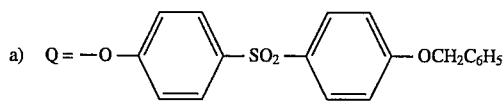
b) Q = 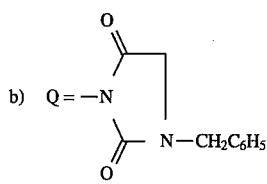
c) Q = 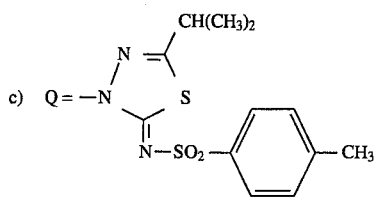
d) Q = 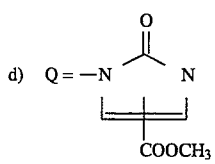
e) Q = 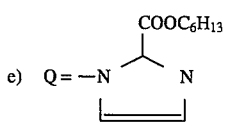
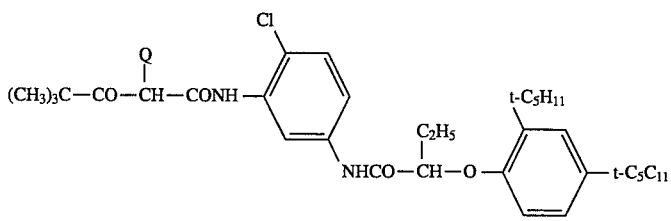
f) Q = 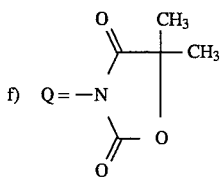
g) Q = 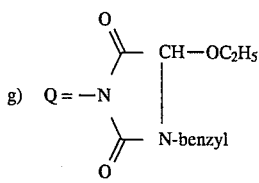

-continued
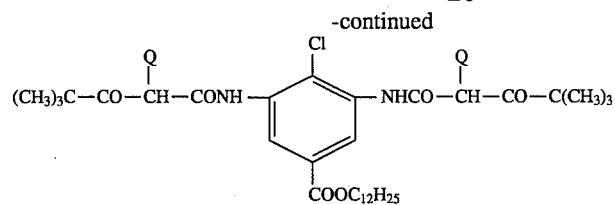
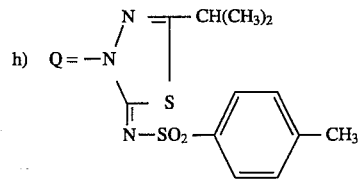
Other examples of yellow couplers are given in U.S. Pat. Nos. 2,407,210, 2,778,658, 2,875,057, 2,908,513, 2,908,573, 3,227,155, 3,227,550, 3,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752 and 4,022,620, DE-A 1 547 868, 2 057 941, 2 162 899, 2 163 813, 2 213 461, 2 219 917, 2 261 361, 2 261 362, 2 263 875, 2 329 587, 2 414 006 and 2 422 812, GB-A 1 425 020 and 1 077 874, JP-A-88/123 047 and EP-A-447 969.
The yellow couplers are usually used in an amount of from 0.05 to 2 mol, preferably from 0.1 to 1 mol, per mol of silver halide.
Typical and preferred yellow couplers conform to the formulae:
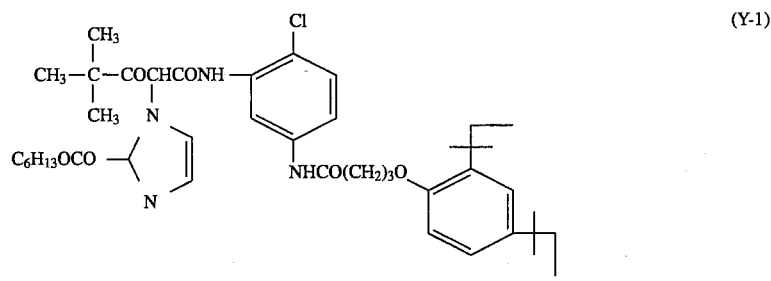
(Y-1)
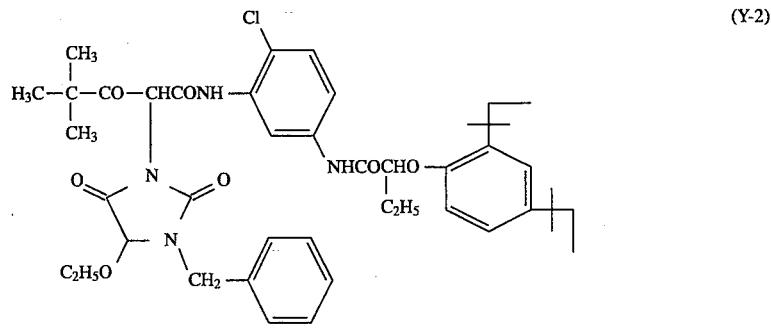
(Y-2)
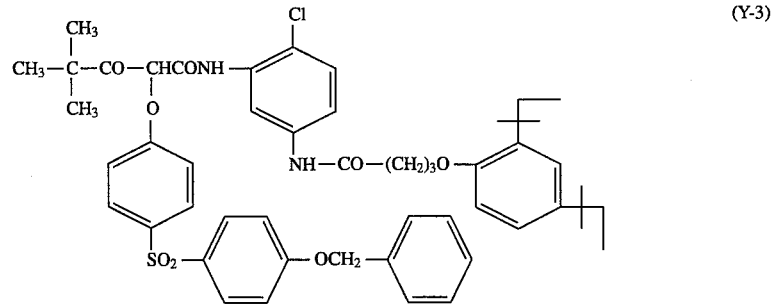
(Y-3)

-continued
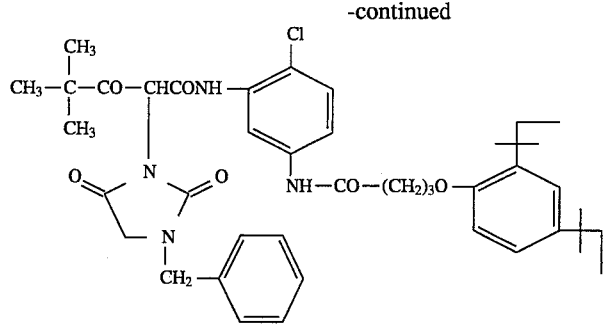 (Y-4)
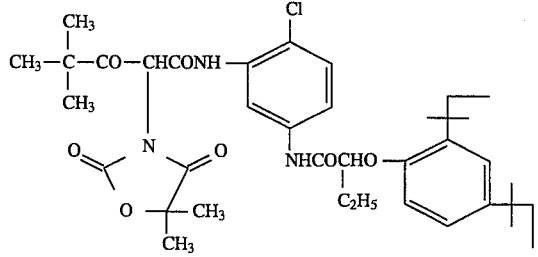 (Y-5)
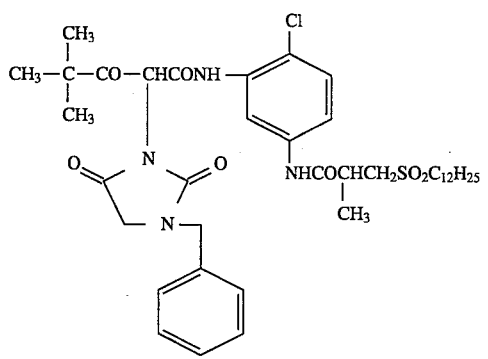 (Y-6)
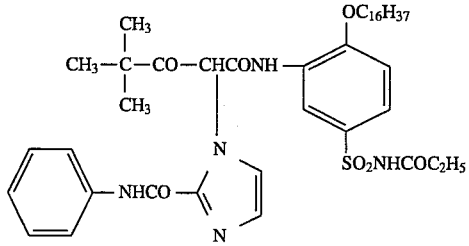 (Y-7)
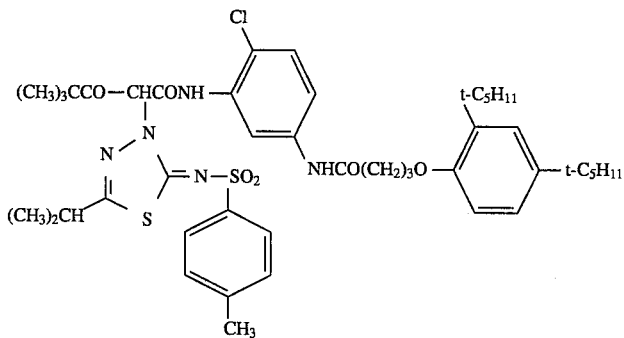 (Y-8)

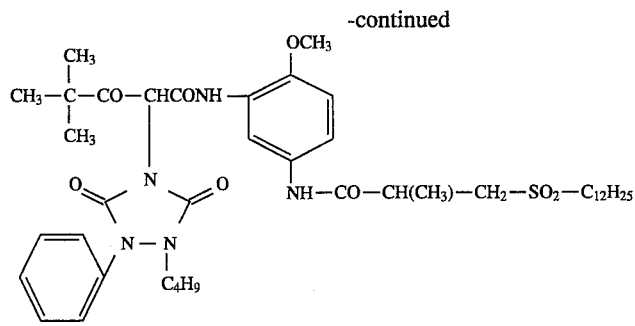
(Y-9)

Magenta couplers can be, for example, single 1-aryl-5-pyrazolones, or pyrazole derivatives which have been condensed with 5-membered heterocyclic rings, for example imidazopyrazoles, pyrazolopyrazoles, pyrazolotfiazoles or pyrazolotetrazoles.

A group of magenta couplers comprises 5-pyrazolones of the formula C

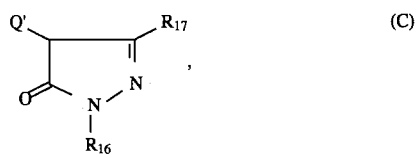

as described in British Patent 2 003 473. In this formula, $R_6$ is hydrogen, alkyl, aryl, alkenyl or a heterocyclic group, $R_{17}$ is hydrogen, alkyl, aryl, a heterocyclic group, an ester group, alkoxy, alkylthio, carboxyl, arylamino, acylamino, (thio)urea, (thio)carbamoyl, guanidino or sulfonamido.

$R_{17}$ is preferably a

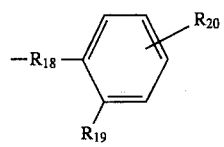

group in which $R_{18}$ is imino, acylamino or ureido, $R_{19}$ is hydrogen, halogen, alkyl or alkoxy, and $R_{20}$ is hydrogen, alkyl, acylamino, carbamoyl, sulfamoyl, sulfonamido, alkoxycarbonyl, acyloxy or urethane.

If Q' is hydrogen, the magenta coupler is tetra-equivalent with respect to the silver halide.

Typical examples of magenta couplers of this type are compounds of the formula

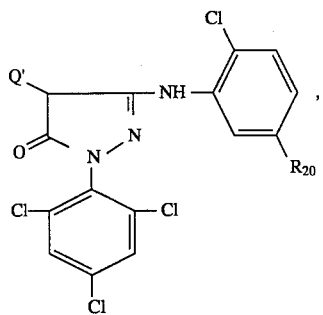

in which $R_{20}$ is as defined above, and Q', as described above, is a leaving group. These compounds are preferably in the novel material.

Further examples of tetra-equivalent magenta couplers of this type are given in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500, and JP-A-89/309 058.

If Q' in the formula C is not hydrogen, but instead a group which is eliminated during the reaction with the oxidized developer, the magenta coupler is diequivalent. In this case, Q can be, for example, halogen or a group bonded to the pyrazole ring via O, S or N. Such di-equivalent couplers give increased colour density and are more reactive toward the oxidized developer than corresponding tetraequivalent magenta couplers.

Examples of di-equivalent magenta couplers are described in U.S. Pat. Nos. 3,006,579, 3,419,391, 3,311,476, 3,432,521, 3,214,437, 4,032,346, 3,701,783, 4,351,897, 3,227,554, EP-A-133 503, DE-A-2 944 601, JP-A-78/34 044, 74/53 435, 74/53 436, 75/53 372 and 75/122 935.

Typical and preferred magenta couplers conform to the formulae

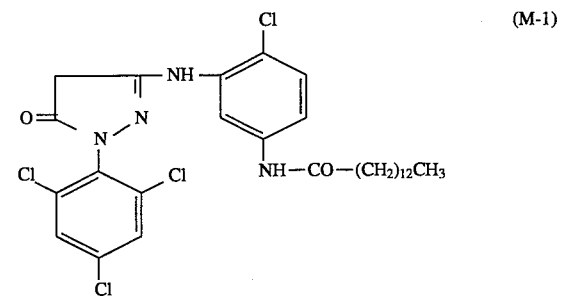
(M-1)

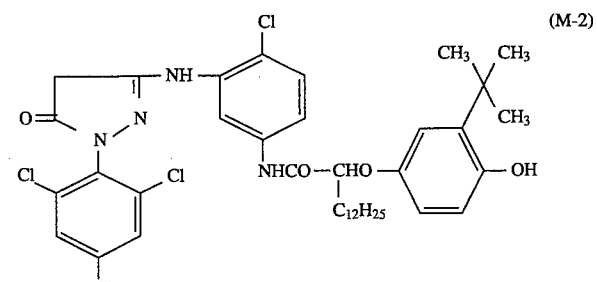
(M-2)

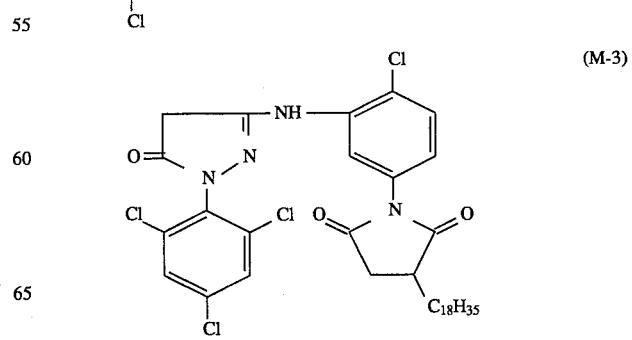
(M-3)

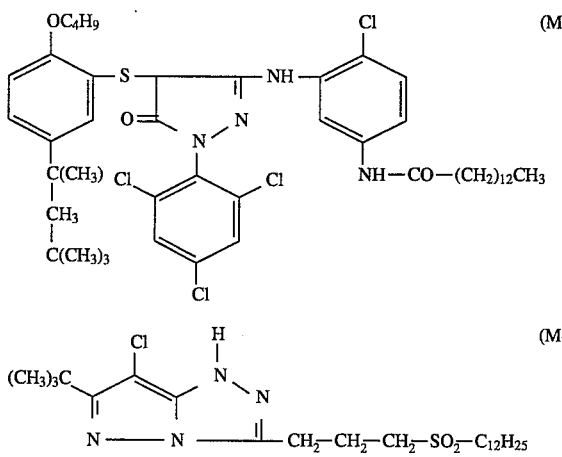
(M-4)

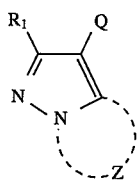
(M-5)

2 pyrazolone rings can be linked via a divalent Q', giving so-called bis-couplers. These are described, for example, in U.S. Pat. Nos. 2,632,702, 2,618,864, GB-A-968 461, GB-A-786 859, JP-A-76/37 646, 59/4086, 69/16 110, 69/26 589, 74/37 854 and 74/29 638. Y is preferably an O-alkoxyarylthio group.

As mentioned above, the magenta couplers can also be pyrazoles which have been condensed with 5-membered heterocyclic tings, so-called pyrazoloazoles. Their advantages over simple pyrazoles is that they have colours of greater formalin resistance and purer absorption spectra.

Magents couplers of the pyrazoloazole type, which are likewise preferred, can be represented by the formula

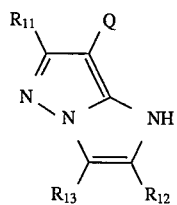
(M-7)

in which $R_1$ is hydrogen or a substituent, Z represents the non-metallic atoms necessary to complete a 5-membered ring containing 2 or 3 nitrogen atoms, it being possible for this ring to be substituted, and Q is hydrogen or a leaving group.

Of these, preference is given to magenta couplers of the formulae

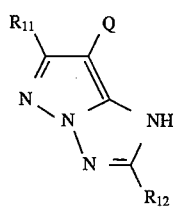
(M-8)

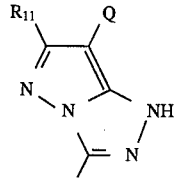
(M-9)

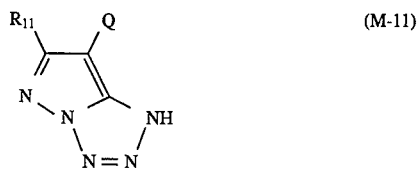
(M-10)

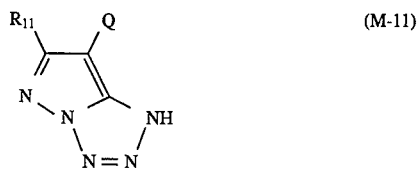
(M-11)

in which $R_{11}$, $R_{12}$ and $R_{13}$, independently of one another, are, for example, hydrogen, halogen, a group of the formula —$CR_3$, in which the radicals R, independently of one another, are hydrogen or alkyl, aryl, heterocyclyl, cyano, hydroxyl, nitro, carboxyl, amino, alkoxy, aryloxy, acylamino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclyloxy, azo, acyloxy, carbamoyloxy, silyloxy, aryloxycarbonylamino, imido, heterocyclic thio, sulfinyl, phosphonyl, aryloxycarbonyl, acyl or azolyl, preferably hydrogen; halogen (for example chlorine or bromine), a group of the formula —$CR_3$, in which the radicals R, independently of one another, are hydrogen or alkyl, aralkyl, alkenyl, alkynyl, cycloalkyl or cycloalkenyl, particularly preferably methyl, ethyl, propyl, isopropyl, t-butyl, tridecyl, 2-methanesulfonylethyl, 3-(3-pentadecylphenoxy)propyl, 3-(4-(2-(4-(4-hydroxyphenylsulfonyl)phenoxy)dodecanamido)phenyl)propyl 2-ethoxytridecyl, trifluoromethyl, cyclopentyl, 3-(2,4-di-t-amylphenoxy)propyl; aryl (for example phenyl, 4-t-butylphenyl, 2,4-di-t-amylphenyl or 4-tetradecaneamidophenyl); heterocyclyl (for example 2-furyl, 2-thienyl, 2-pyrimidinyl or 2-benzothiazolyl); cyano; hydroxyl, nitro; carboxyl; amino; alkoxy (for example methoxy, ethoxy, 2-methoxyethoxy; 2-dodecylethoxy or 2-methanesulfonylethoxy); aryloxy (for example phenoxy, 2-methylphenoxy, 4-t-butylphenoxy, 3-nitrophenoxy, 3-t-butoxycarbamoylphenoxy or 3-methoxycarbamoyl); acylamino (for example acetoamido, benzamido, tetradecanamido, 2-(2,4-di-t-amylphenoxy)butanamido, 4-(3-t-butyl-4-hydroxyphenoxy)butanamido or 2-(4-(4-hydroxyphenylsulfonyl)phenoxy)decanamido); methylbutylamino); anilino (for example phenylamino, 2-chloroanilino, 2-chloro-5-tetradecanaminoanilino, 2-chloro-5-dodecyloxycarbonylanilino, N-acetylanilino or 2-chloro-5-(alpha-(3-t-butyl-4-hydroxyphenoxy)dodecanamidoanilino); ureido (for example phenylureido, methylureido or N,N-dibutylureido); sulfamoylamino (for example N,N-dipropylsulfamoylamino or N-methyl-N-decylsulfamoylamino); alkylthio (for example methylthio, octylthio, tetradecylthio, 2-phenoxyethylthio, 3-phenoxypropylthio or 3-(4-t-butylphenoxy)propylthio); arylthio (for example phenylthio, 2-butoxy-5-t-octylphenylthio, 3-pentadecylphenylthio, 2-carboxyphenylthio or 4-tetradecanamidophenylthio); alkoxycarbonylamino (for example methoxycarbonylamino or tetradecyloxycarbonylamino); sulfonamido (for example methanesulfonamido, hexadecanesulfonamido, benzenesulfonamido, p-toluenesulfonamido, octadecanesulfonamido or 2-methoxy-5-t-butylbenzenesulfonamido); carbamoyl (for example N-ethylcarbamoyl, N,N-dibutylcarbamoyl, N-(2-dodecyloxyethyl)carbamoyl, N-methyl-N-dodecylcarbamoyl or N-(3-(2,4-di-t-amylphenoxy)propyl)carbamoyl); sulfamoyl (for example N-ethylsulfamoyl, N,N-dipropylsulfamoyl, N-2(-dodecyloxyethyl)sulfamoyl, N-ethyl-N-dodecylsulfamoyl or N,N-diethylsulfamoyl); sulfonyl (for example methanesulfonyl, octanesulfonyl, benzenesulfonyl or toluenesulfonyl); alkoxycarbonyl (for example methoxycarbonyl, butoxycarbonyl, dodecyloxycarbonyl or octadecyloxycarbonyl); heterocyclyloxy (for example 1-phenyltetrazol-5-oxy or 2-tetrahydropyranyloxy); azo (for example phenylazo, 4-methoxyphenylazo, 4-pivaloylaminophenylazo or 2-hydroxy-4-propanoylphenylazo); acyloxy (for example acetoxy); carbamoyloxy (for example N-methylcarbamoyloxy or N-phenylcarbamoyloxy); silyloxy (for example trimethylsilyloxy or dibutylmethylsilyloxy); aryloxycarbonylamino (for example phenoxycarbonylamino); imido (for example N-succinimido, N-phthalimido or 3-octadecenylsuccinimido); heterocyclylthio(for example 2-benzothiazolylthio, 2,4-diphenoxy-1,3,5-triazole-6-thio or 2-pyridylthio); sulfinyl (for example dodecanesulfinyl, 3-pentadecylphenylsulfinyl or 3-phenoxypropylsulfinyl); phosphonyl (for example phenoxyphosphonyl, octyloxyphosphonyl or phenylphosphonyl); aryloxycarbonyl (for example phenoxycarbonyl); acyl (for example acetyl, 3-phenylpropanoyl, benzoyl or 4-dodecyloxybenzoyl); or azolyl (for example imidazolyl, pyrazolyl or 3-chloropyrazol-1-yl).

These substituents may, if desired, be further substituted, for example by halogen or by an organic radical bonded via a C, O, N or S atom.

Preferred groups R11 are alkyl, aryl, alkoxy, aryloxy, alkylthio, ureido, urethane and acylamino groups.

$R_{12}$ can be as defined for R and is preferably hydrogen, alkyl, aryl, a heterocyclic ring, alkoxycarbonyl, carbamoyl, sulfamoyl, sulfinyl, acyl or cyano.

$R_{13}$ can be as defined for R and is preferably hydrogen, alkyl, aryl, heterocyclyl, alkoxy, aryloxy, alkylthio, arylthio, alkoxycarbonyl, carbamoyl or acyl, in particular alkyl, aryl, heterocyclyl, alkylthio or arylthio.

Q is hydrogen or a leaving group such as halogen, alkoxy, aryloxy, acyloxy, alkyl- or arylsulfonyloxy, acylamino, alkyl- or arylsulfonamido, alkoxycarbonyloxy, aryloxycarbonyloxy, alkyl-, aryl- or heterocyclyl-S-carbamoylamino, a 5- or 6-membered, nitrogen-containing heterocyclic radical, imido or arylazo. These groups are unsubstituted or further substituted as indicated for $R_{11}$.

Q is preferably halogen (for example fluorine, chlorine or bromine); alkoxy (for example ethoxy, dodecyloxy, methoxyethylcarbamoylmethoxy, carboxypropoxy, methylsulfonylethoxy or ethoxycarbonylmethoxy); aryloxy (for example 4-methylphenoxy, 4-chlorophenoxy, 4-methoxyphenoxy, 4-carboxyphenoxy, 3-ethoxycarboxyphenoxy, 3-acetylaminophenoxy or 2-carboxyphenoxy); acyloxy (for example acetoxy, tetradecanoyloxy or benzoyloxy); alkyl- or arylsulfonyloxy (for example methanesulfonyloxy or toluenesulfonyloxy); acylamino (for example dichloroacetylamino or heptafluorobutyrylamino); alkyl- or arylsulfonamido (for example methanesulfonamido, trifluoromethanesulfonamido or p-toluenesulfonylamido); alkoxycarbonyloxy (for example ethoxycarbonyloxy or benzyloxycarbonyloxy); aryloxycarbonyloxy (for example phenoxycarbonyloxy); alkyl-, aryl- or heterocyclyl-S- (for example dodecylthio, 1-carboxydodecylthio, phenylthio, 2-butoxy5-t-octylphenylthio or tetrazolylthio); carbamoylamino (for example N-methylcarbamoylamino or N-phenylcarbamoylamino); a 5- or 6-membered, nitrogen-containing ring (for example imidazolyl, pyrazolyl, triazolyl, tetrazolyl or 1,2-dihydro-2-oxo-1-pyridyl); imido (for example succinimido or Hydantoinyl); or arylazo (for example phenylazo or 4-methoxyphenylazo).

Q can also form corresponding bis-compounds by condensation of tetraequivalent couplers with an aidehyde or ketone. Furthermore, Q can contain photographically active groups, such as development inhibitors or development accelerators. Q is preferably halogen, alkoxy, aryloxy, alkyl- or arylthio, or a 5- or 6-membered, nitrogen-containing heterocyclic group which is bonded to the coupling site via a nitrogen atom.

Pyrazolotetrazoles are described in JP-A-85/33 552; pyrazolopyrazoles are described in JP-A-85/43 695; pyrazoloimidazoles are described in JP-A-85/35 732, JP-A-86/18 949 and U.S. Pat. No. 4,500,630; pyrazolotriazoles are described in JP-A-85/186 567, JP-A-86/47 957, JP-A-85/215 687, JP-A-85/197 688, JP-A-85/172 982, EP-A-119 860, EP-A-173 256, EP-A-178 789, EP-A-178 788 and in Research Disclosure 84/24 624.

Other pyrazoloazole magenta couplers are described in: JP-A-86/28 947, JP-A-85/140 241, JP-A-85/262 160, JP-A-85/213 937, JP-A-87/278 552, JP-A-87/279 340, JP-A-88/100 457, EP-A-177 765, EP-A-176 804, EP-A-170 164, EP-A-164 130, EP-A-178 794, DE-A-3 516 996, DE-A-3 508 766 and Research Disclosure 81/20 919, 84/24 531 and 85/25 758.

Suitable examples of such couplers are:

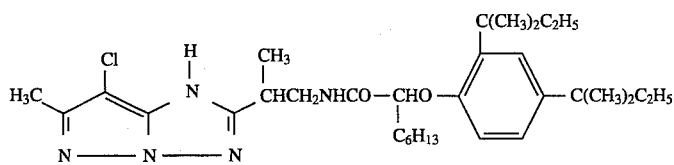

(M-6)

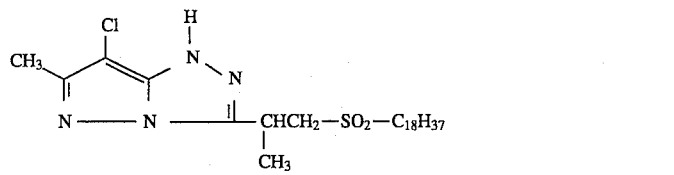

(M-12)

-continued
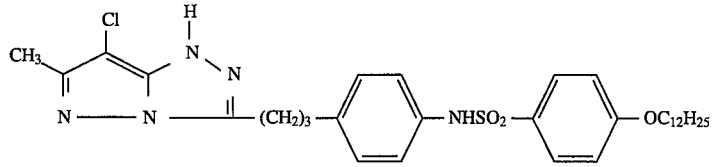
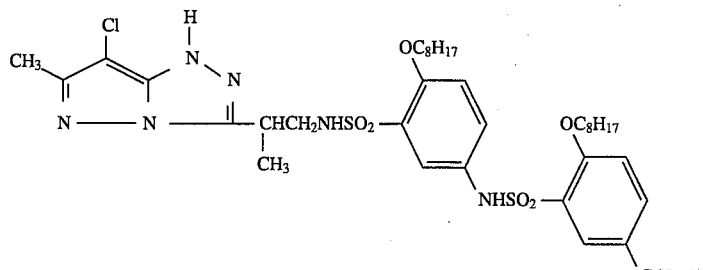
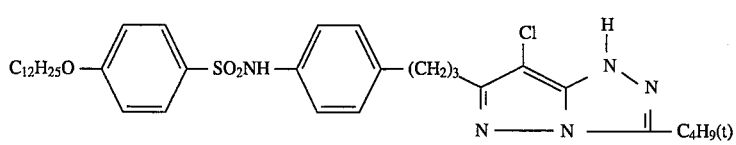
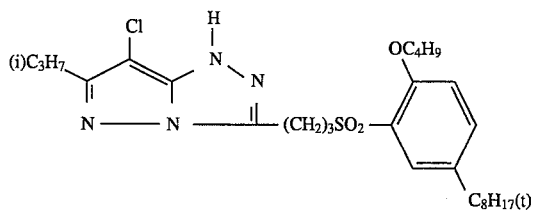
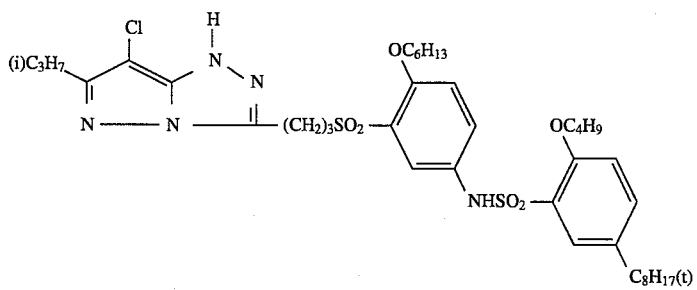
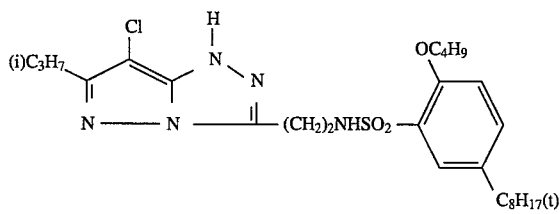
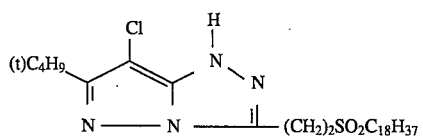
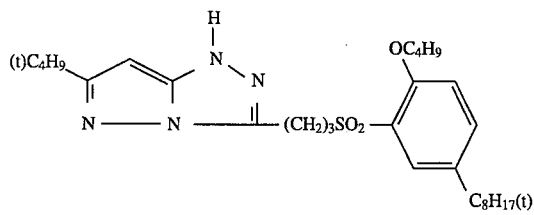

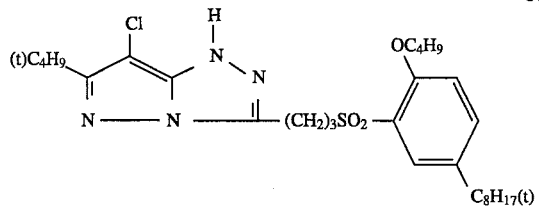
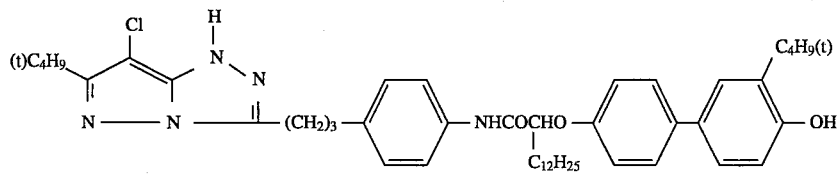
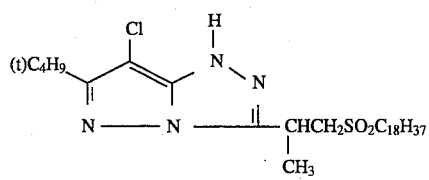
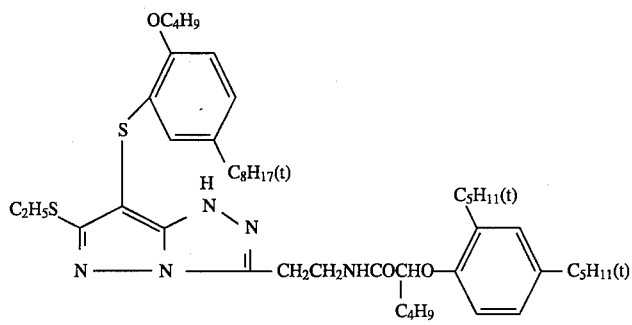
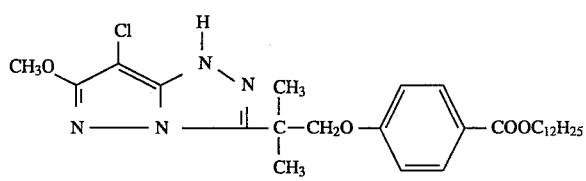
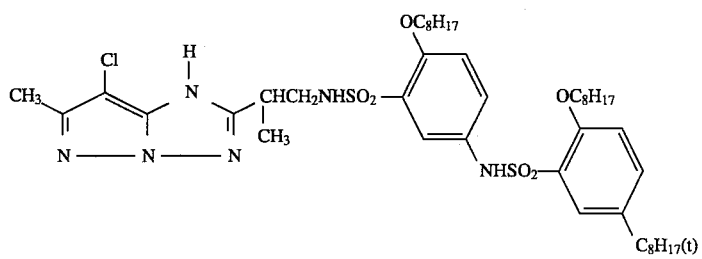
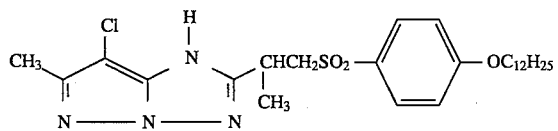
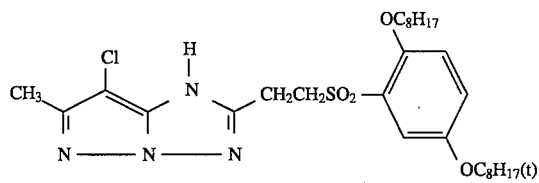

-continued
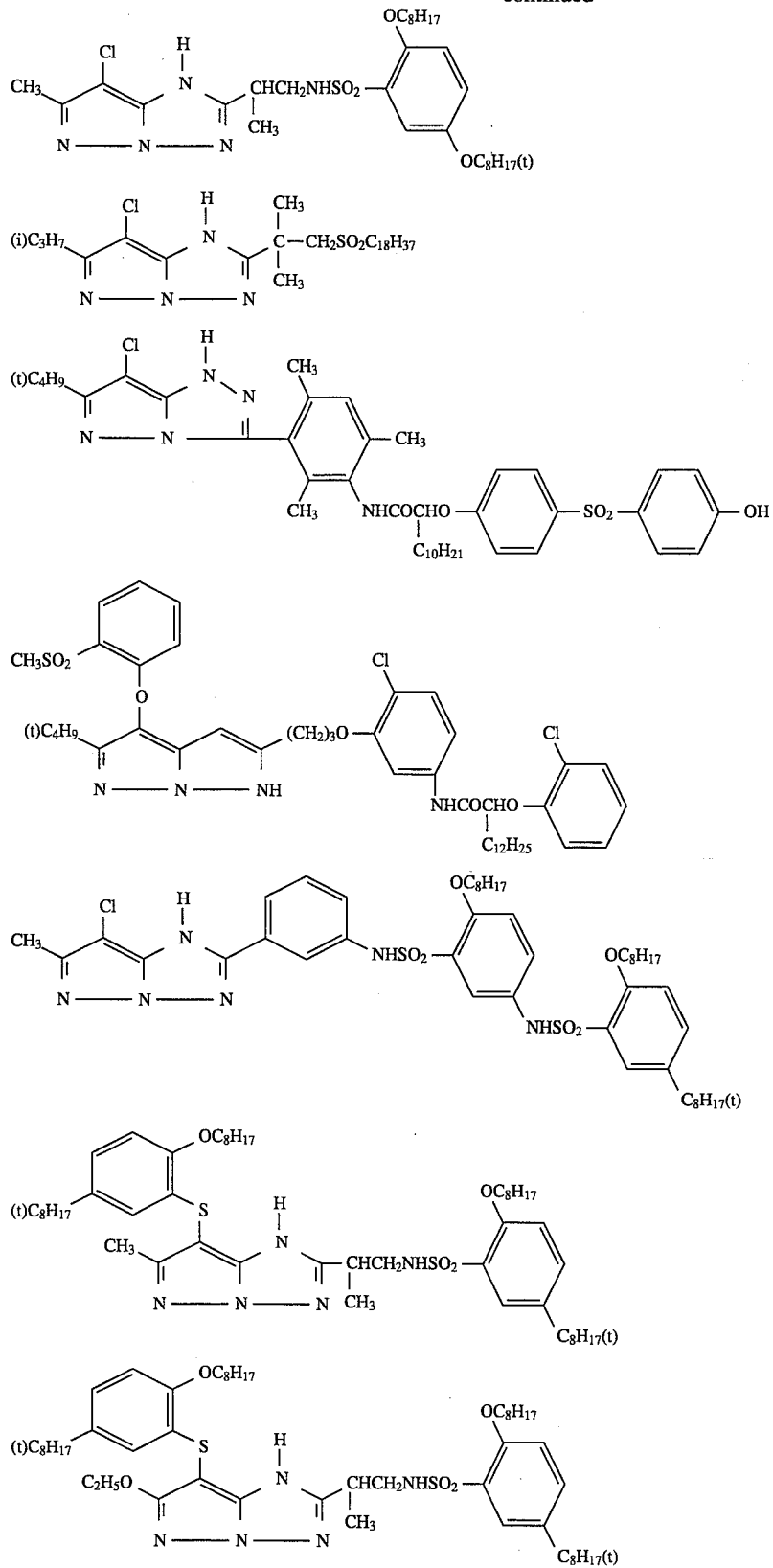

-continued
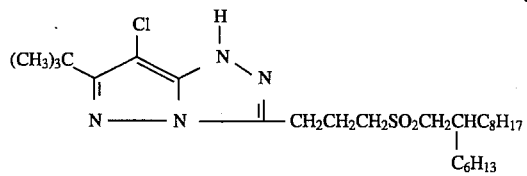
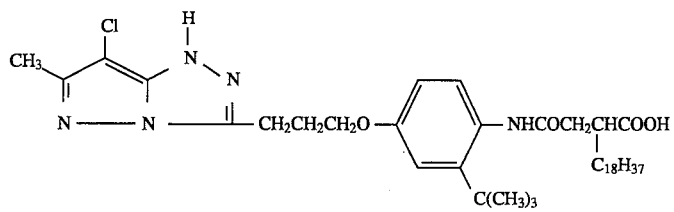
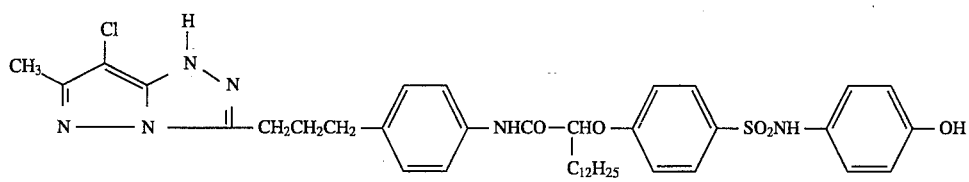
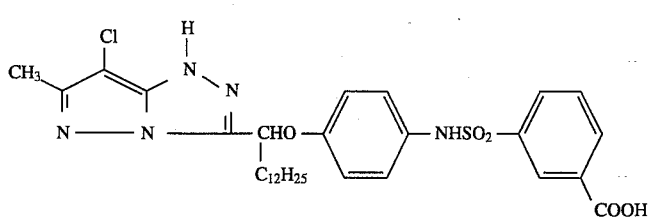
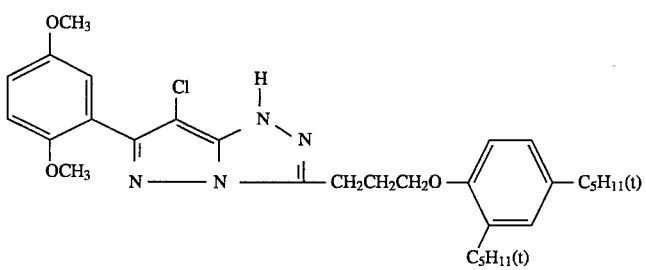
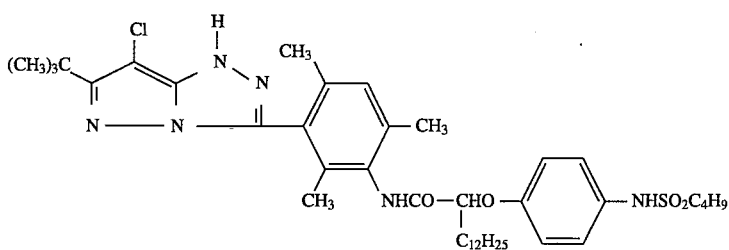
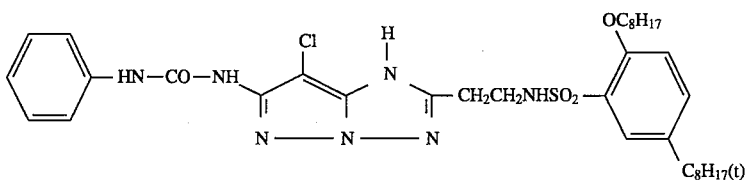
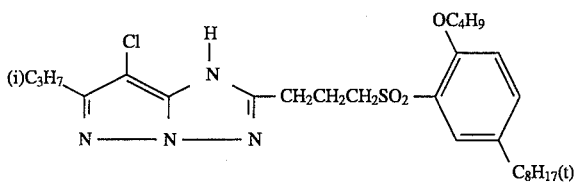

-continued
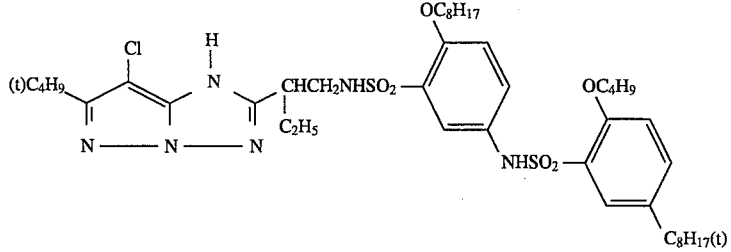
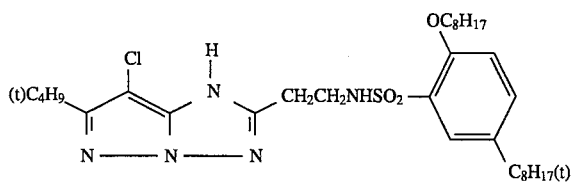
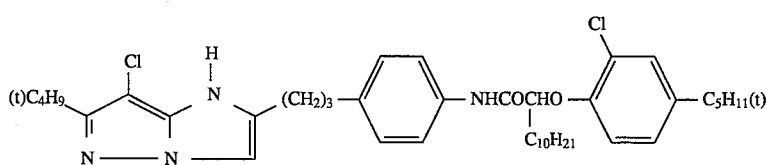
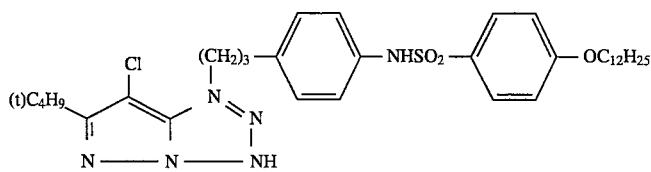
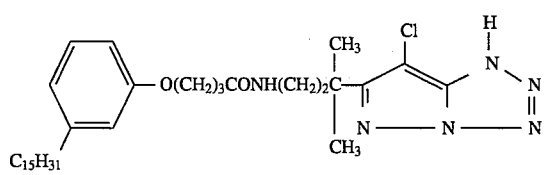
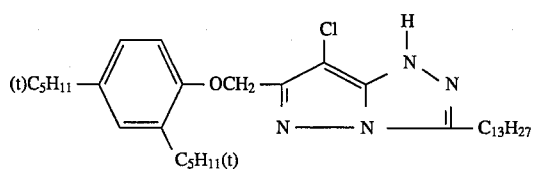
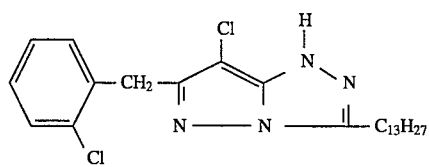
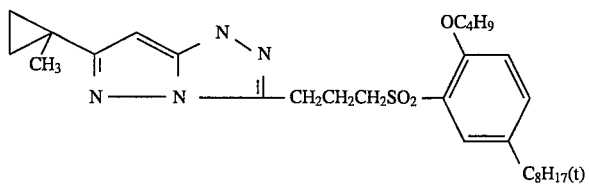
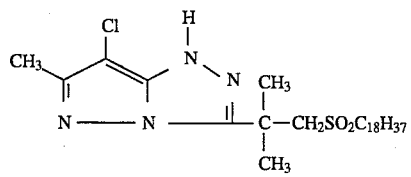

-continued
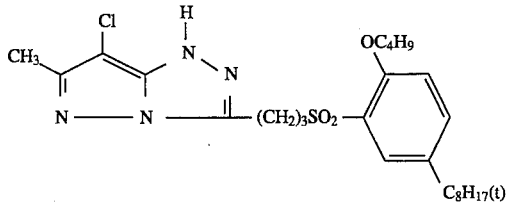
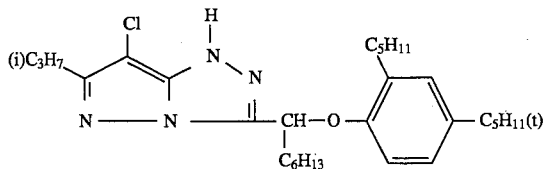
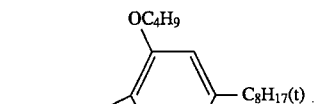
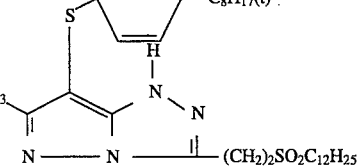
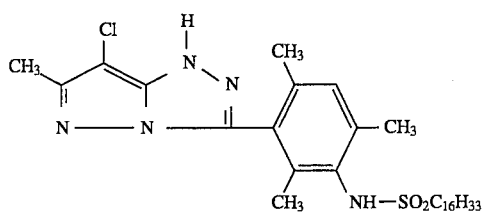
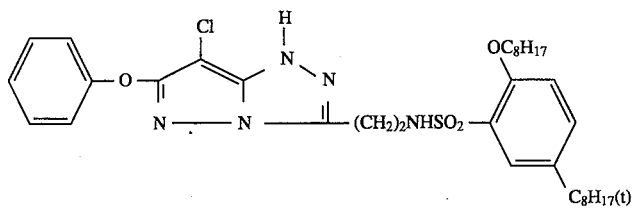
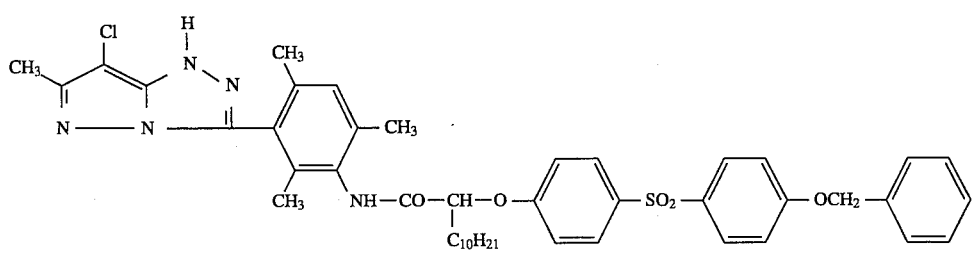
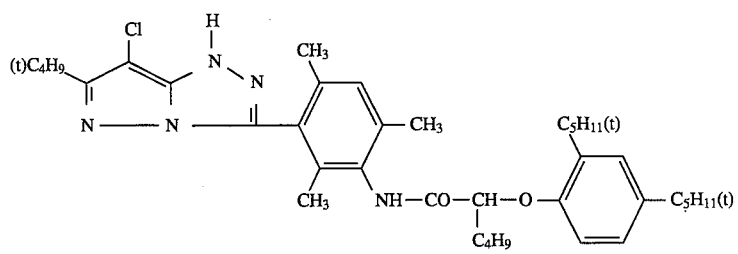

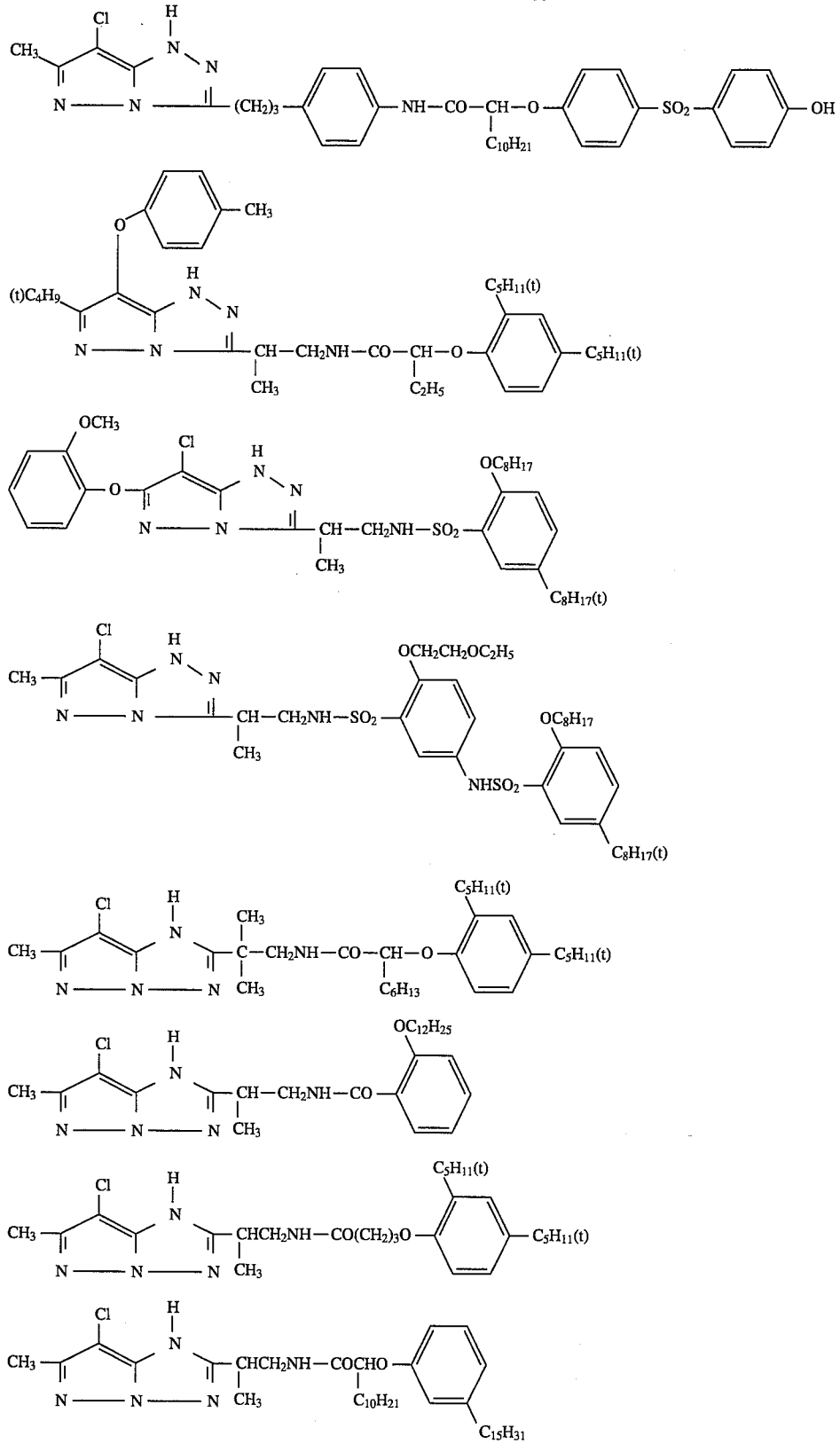

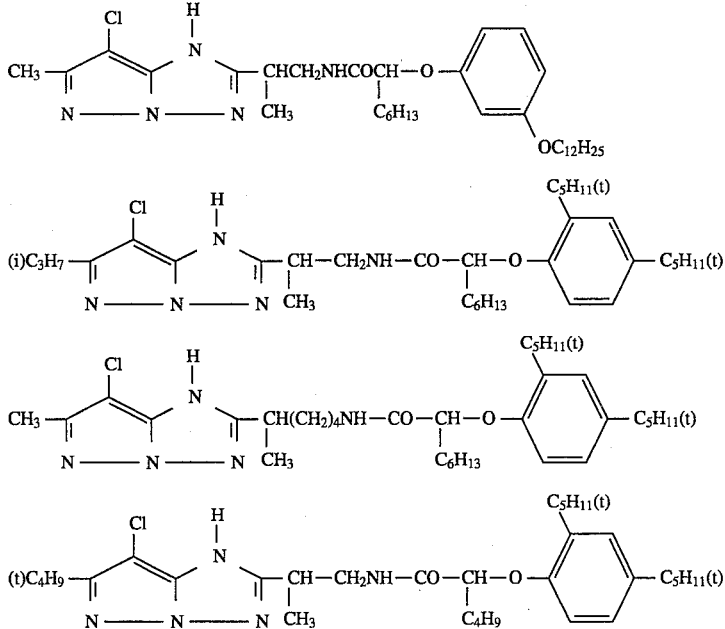

Cyan couplers can be, for example, derivatives of phenol, of 1-naphthol or of pyrazoloquinazolone. Preference is given to structures of the formula E,

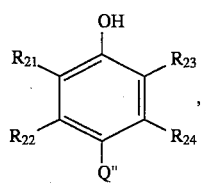
(E)

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, $R_{22}$ is preferably an alkyl or amino group. $R_{23}$ is preferably an amino group, and $R_{24}$ is preferably hydrogen. Q" is hydrogen or a leaving group which is eliminated during the reaction with the oxidized developer. A detailed list of cyano couplers is given in U.S. Pat. No. 4,456,681.

Examples of customary cyan couplers are the following:

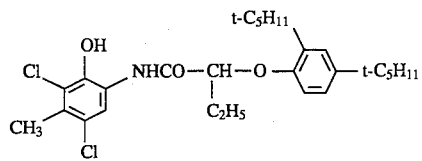
(E-1)

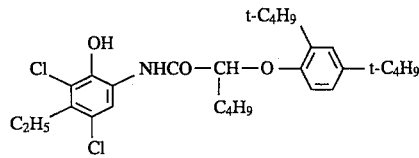
(E-2)

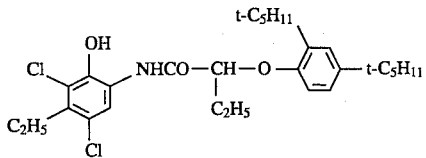
(E-3)

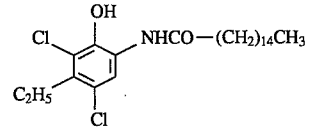
(E-4)

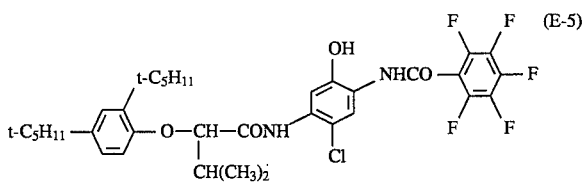
(E-5)

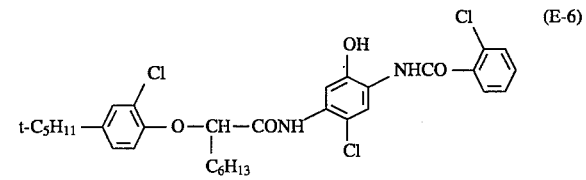
(E-6)

Further examples of cyan couplers are given in the following: U.S. Pat. Nos. 2,369,929, 2,423,730, 2,434,272, 2,474,293, 2,521,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086, 4,456,681, 4,873,183 and 4,923,791, and EP-A-354 549 and EP-A-398 664.

Preference is given in the red-sensitive silver-halide emulsion layer of the novel material to cyan couplers of the formula

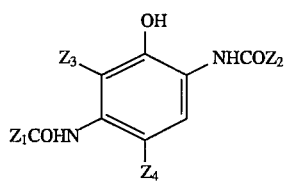

(E-7)

and/or of the formula

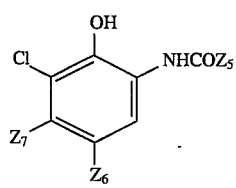

(E-8)

in which $Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group, and $Z_7$ is alkyl.

The colour developers usually used for colour-photographic materials are p-dialkylaminoanilines. Examples thereof are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hyddroxyethylaniline, 3-methyl-4-amino-N-ethyl-N-α-hydroxyethylaniline, 3-methyl-4-amino-N-ethyl-N-α-methanesulphonamidoethylaniline, 3-methyl-4-amino-N-ethyl-N-α-methooxyethyl-aniline, 3-α-methanesulphonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α'-(α''-methoxyethoxy)ethoxy]ethyl-3-methyl- 4-aminoaniline, N-ethyl-N-α-(α'-methoxyethoxy)ethyl-3-methyl-4-aminoaniline, and the salts of such compounds, for example sulfates, hydrochlorides or toluenesulfonates.

The UV absorbers of the formula (I) and (HI) used according to the invention can be incorporated, alone or together with the colour coupler and, if desired, further additives, into the colour-photographic material by pre-dissolving them in high-boiling organic solvents. Preference is given to solvents which boil at above 160° C. Typical examples of such solvents are the esters of phthalic acid, phosphoric acid, citric acid, benzoic acid or of fatty acids, and alkylamides and phenols.

A low-boiling solvent is usually used in addition in order to simplify incorporation of the additives into the colour-photographic material. Examples of such solvents are esters, for example ethyl acetate, alcohols, for example butanol, ketones, for example methyl isobutyl ketone, chlorinated hydrocarbons, for example methylene chloride, or amides, for example dimethylformamide. If the additives are themselves liquid, they can also be incorporated into the photographic material without the aid of solvents.

The novel UV absorbers can, if desired, be dispersed in the gelatine layer without oil; Research Disclosure 88/296 017 and 89/303 070.

Further details of high-boiling solvents which can be used are given in the following publications:

Phosphates: GB-A-791 219, BE-A-755 248, JP-A-76/76 739, 78/27 449, 78/218 252, 78/97 573, 79/148 133, 82/216 177, 82/93 323 and 83/216 177 and EP-A-265 296.

Phthalates: GB-A-791 219, JP-A-77/98 050, 82/93 322, 82/216 176, 82/218 251, 83/24 321, 83/45 699, 84/79 888.

Amides: GB-A-791 129, JP-A-76/105 043, 77/13 600, 77/61 089, 84/189 556, 87/239 149, U.S. Pat. No. 928 741, EP-A-270 341, WO 88/00 723

Phenols: GB-A-820 329, FR-A-1 220 657, JP-A-69/69 946, 70/3818, 75/123 026, 75/82 078, 78/17 914, 78/21 166, 82/212 114 and 83/45 699.

Other oxygen-containing compounds: U.S. Pat. No. 3,748,141, 3,779,765, JP-A-73/75 126, 74/101 114, 74/10 115, 75/101 625, 76/76 740, 77/61 089, EP-A-304 810 and BE-A-826 039.

Other compounds: JP-A-72/115 369, 72/130 258, 73/127 521, 73/76 592, 77/13 193, 77/36 294, 79/95 233, 91/2748, 83/105 147 and Research Disclosure 82/21 918.

The amount of high-boiling solvent is, for example, in the ratio of 50 mg to 2 g, preferably from 200 mg to 1 g, per m² of support.

The photographic layers may furthermore contain colour-cast inhibitors. These prevent the formation of colour casts, as formed, for example, due to reaction of the coupler with unintentionally oxidized developer or with by-products of the colour-formation process. Such colour-cast inhibitors are usually hydroquinine derivatives, but can also be derivatives of aminophenols, of gallic acid or of ascorbic acid. Typical examples thereof are given in the following publications: U.S. Pat. NO. 2,360,290, 2,336,327, 2,403,721, 2,418,613, 2,675,314, 2,701,197, 2,704,713, 2,728,659, 2,732,300, 2,735,365; EP-A-124 877, EP-A-277 589, EP-A-338 785; JP-A-75/92 988, 75/92 989, 75/93 928, 75/110 337, 84/5247 and 77/146 235.

The photographic layers can also contain DIR couplers (DIR means Development Inhibition Release), which give colourless compounds with the oxidized developer. They are added to improve the sharpness and grain of the colour images.

The photographic layers in the novel material may also contain further UV absorbers. Examples of such UV absorbers are benzotriazoles, 2-hydroxybenzophenones, salicylic acid esters, acrylonitrile derivatives or thiazolines. These UV absorbers are described in greater detail, for example, in the following publications: U.S. Pat. Nos. 3,314,794, 3,352, 681, 3,705,805, 3,707,375, 4,045,229, 3,700,455, 3,533,794, 3,698,907, 3,705,805, 3,738,837, 3,762,272, 4,163,671, 4,195,999, 4,309,500, 4,431,726, 4,443,543, 4,576,908, 4,749,643,-GB-A-1 564 089, EP-A-190 003 and JP-A-71/ 2784, 81/111 826, 81/27 146, 88/53 543 and 88/55 542. Preferred UV absorbers are benzotriazoles, in particular 2-(2-hydroxyphenyl) benzotriazoles.

The photographic layers may also contain phenolic compounds which act as light stabilizers for the colour image and as colour-cast inhibitors. They may be present in a photosensitive layer (colour layer) or in an interlayer, alone or together with other additives. Such compounds are described in greater detail, for example, in the following publications: U.S. Pat. Nos. 3,700,455, 3,591,381, 3,573, 052, 4,030,931, 4,174,220, 4,178,184, 4,228,235, 4,279,990, 4,346,165, 4,366,226, 4,447,523, 4,528,264, 4,581,326, 4,562,146, 4,559,297, GB-A-1 309 277, 1 547 302, 2 023 862, 2 135 788, 2 139 370, 2 156 091; DE-A-2 301 060, 2 347 708, 2 526 468, 2 621 203, 3 323 448; DD-A-200 691,214 468; EP-A-106 799, 113 124, 125 522, 159 912, 161 577, 164 030, 167 762, 176 845,246 766, 320 776; JP-A-74/134 326, 76/127 730, 76/30 462, 77/3822, 77/154 632, 78/10 842, 79/48 535, 79/70 830, 79/73 032, 79/147 038, 79/154 325, 79/155 836, 82/142 638, 83/224 353, 84/5246, 84/72 443, 84/87 456, 84/192 246, 84/192 247, 84/204 039, 84/204 040, 84/212 837, 84/220 733, 84/222

836, 84/228 249, 86/2540, 86/8843, 86/18 835, 86/18 836, 87/11 456, 87/42 245, 87/62 157, 86/6652, 89/137 258 and in Research Disclosure 79/17 804.

The photographic layers may also contain certain phosphorus(III) compounds, in particular phosphites and phosphonites. These function as light stabilizers for the colour images and as dark-storage stabilizers for magenta couplers. They are preferably added to the high-boiling solvents, together with the coupler. Such phosphorus(III) compounds are described in greater detail, for example, in the following publications: U.S. Pat. Nos. 4,407,935, 4,436,811, 4,956,406, EP-A-181 289, JP-A-73/32 728, JP-A-76/1420 and JP-A-55/66 741.

The photographic layers may also contain organometallic complexes which are light stabilizers for the colour images, in particular for the magenta dyes. Such compounds and combinations thereof with other additives are described in greater detail, for example, in the following publications: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165, 4,590,153; JP-A-81/167 138, 81/168 652, 82/30 834, 82/161 744; EP-A-137 271,161 577, 185 506; DE-A-2 853 865.

The photographic layers may also contain hydroquinone compounds. These function as light stabilizers for the colour couplers and for the colour images and as scavengers of oxidized developer in interlayers. They are used, in particular, in the magenta layer. Such hydroquinone compounds and combinations thereof with other additives are described in greater detail, for example, in the following publications: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572, 4,559,297, FR-A-885 982; GB-A-891 158, 1 156 167, 1 363 921, 2 022 274, 2 066 975, 2 071 348, 2 081 463, 2 117 526, 2 156 091; DE-A-2 408 168, 2 726 283, 2 639 930, 2 901 520, 3 308 766, 3 320 483, 3 323 699; DD-A-216 476, 214 468,214 469, EP-A-84 290, 110 214, 115 305, 124 915, 124 877, 144 288, 147 747, 178 165, 161 577; JP-A-75/33 733, 75/21 249, 77/128 130, 77/146 234, 79/70 036, 79/133 131, 81/83 742, 81/87 040, 81/109 345, 83/134 628, 82/22 237, 82/112 749, 83/17 431, 83/21 249, 84/75 249, 84/149 348, 84/182 785, 84/180 557, 84/189 342, 84/228 249, 84/101 650, 79/24 019, 79/25 823, 86/48 856, 86/48 857, 86/27 539, 86/6652, 86/72 040, 87/11 455, 87/62 157, and Research Disclosure 79/17 901, 79/17 905, 79/18 813, 83/22 827 and 84/24 014.

The photographic layers may also contain derivatives of hydroquinone ethers. These compounds function as light stabilizers and are particularly suitable for stabilizing magenta dyes. Such compounds and combinations thereof with other additives are described in greater detail, for example, in the following publications: U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,134,011, 4,273,864, 4,264,720, 4,279,990, 4,332,886, 4,436,165, 4,360,589, 4,416,978, 4,385,111, 4,459,015, 4,559,297; GB-A 1 347 556, 1 366441, 1 547 392, 1 557 237, 2 135 788; DE-A 3 214 567; DD-214 469, EP-A 161 577, 167 762, 164 130, 176 845; JP-A 76/123 642, 77/35 633, 77/147 433, 78/126, 78/10 430, 78/53 321, 79/24 019, 79/25 823, 79/48 537, 79/44 521, 79/56 833, 79/70 036, 79/70 830, 79/73 032, 79/95 233, 79/145 530, 80/21 004, 80/50 244, 80/52 057, 80/70 840, 80/139 383, 81/30 125, 81/151 936, 82/34 552, 82/68 833, 82/204 306 82/204 037, 83/134 634, 83/207 039, 84/60 434, 84/101 650, 84/87 450, 84/149 348, 84/182 785, 86/72 040, 87/11 455, 87/62 157, 87/63 149, 86/2151, 86/6652, 86/48 855, 89/309 058 and Research Disclosure 78/17 051.

Examples of suitable stabilizers for the magenta couplers are:

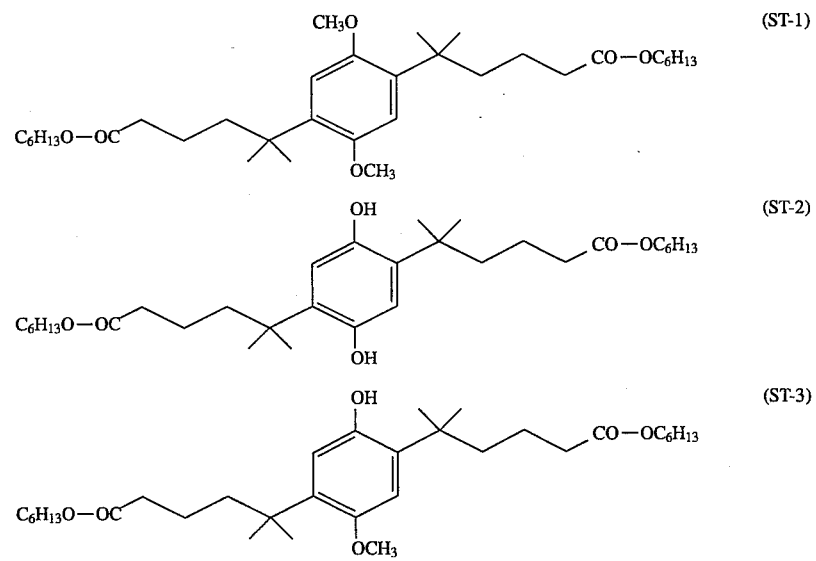

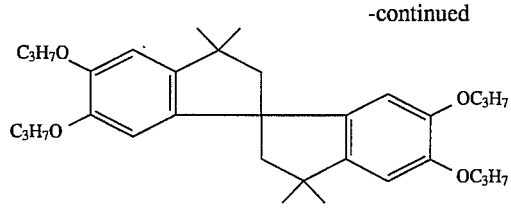 (ST-4)

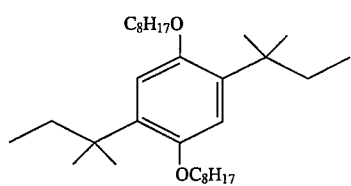 (ST-5)

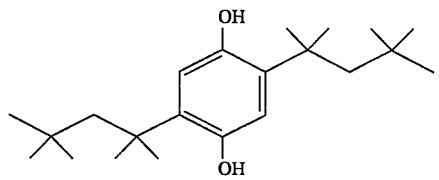 (ST-6)

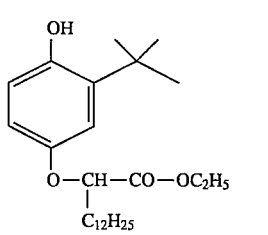 (ST-7)

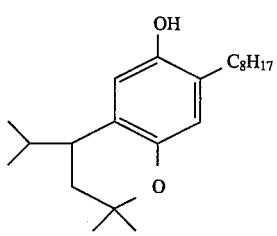 (ST-8)

Silver-halide emulsions which can be used are conventional silver-chloride, silver-bromide or silver-iodide emulsions, or mixtures thereof, such as silver chlorobromide and silver chloroiodide emulsions, in which the silver halides can have any known crystal forms. The use of silver-chloride emulsions is of particular importance in the novel material. The preparation of such emulsions and the sensitization thereof are described in RESEARCH DISCLOSURE, November 1989, No. 307 105. This publication furthermore mentions a number of binders for said emulsions which can also be used in the novel materials. The same applies to the supports mentioned in the publication.

The silver-halide emulsion which can be used for carrying out this invention can be sensitized for all desired wavelengths with the aid of sensitization pigments. These can be cyanine pigments, merocyanine pigments, holopolar pigments, hemicyanine pigments, styryl pigments or hemioxanol pigments.

The photosensitive material may also contain water-soluble dyes, in order, for example, to improve the clarity by preventing radiation damage. These can be oxanol dyes, hemioxanol dyes, styryl dyes, merocyanine dyes, cyanine dyes, anthraquinone dyes and azo dyes.

The novel material can also be combined with further materials, as described, for example, JP-A-87/215 272, 92/9035, 92/21 840 and EP-A-429 240.

The present application also relates to the use of the compounds of the formula (I) for stabilizing ink-jet printing inks, to the stabilized inks, and to the recording material containing the compounds of the formula (I). Preferred compounds of the formula (I) are the compounds mentioned above. Examples of compounds of the formula (I) which can be used are described in greater detail under the photographic materials.

The novel inks are distinguished by good light stability. They can be used, for example, for felt-tip pens, stamp pads, fountain-pen holders and pen plotters, and in offset printing, letterpress printing, flexographic printing and intaglio printing processes, and also in colour ribbons for dot-matrix and letter-quality printing. They are preferably used in ink-jet printing processes.

Printers used in current ink-jet printing processes are divided into continuous ink-jet and drop-on-demand printers, in particular bubble-jet printers. The novel inks can be used for these printers. In particular, ink-jet printing papers and forms are printed.

The novel inks may contain water-soluble solvents, for example mono-, di-, tri- or higher ethylene glycols, propylene glycol, 1,4-butanediol, or ethers of such glycols, thiodiglycol, glycerol and ethers and esters thereof, polyglycerol, mono-, di- and triethanolamine, propanolamine, dimethylformamide, dimethyl sulfoxide, dimethylacetamide, N-methylpyrrolidone, 1,3-dimethylimidazolidone, methanol, ethanol, isopropanol, n-propanol, diacetone alcohol, acetone, methyl ethyl ketone or propylene carbonate.

The novel inks contain dyes, as also known for the dyeing of natural fibres. Examples which may be mentioned are monoazo, disazo or polyazo dyes, reactive dyes, triphenylmethane dyes, xanthene dyes and phthalocyanine dyes. Specific examples thereof are Food Black 2, C.I. Direct Black 19, C.I. Sulphur Black 1, Acid Red 35, Acid Red 14, Acid Red 52, Acid Yellow 17, Acid Yellow 23 and copper phthalocyanines, furthermore Direct Black 38, Direct Black 168, Acid Red 249, Direct Red 227, Direct Yellow 86, Direct Yellow 132, Acid Blue 9, Direct Blue 86, Direct Blue 199, Reactive Red 24, Reactive Red 40 and Reactive Red 159, and the azo dyes mentioned in EP-A-366 121.

The inks may also contain further conventional additives, for example binders, surfactants, biocides, corrosion inhibitors, sequestrants, pH buffers or conductive additives. They may also contain further UV absorbers or light stabilizers, for example the compounds mentioned in U.S. Pat. Nos. 5,073,448, 5,089,050 or in particular in U.S. Pat. Nos. 5,096,489 and 5,124,723. In general, however, the novel addition of a stabilizer of the formula (I) is sufficient to stabilize the inks.

Also known are ink-jet printing inks which comprise more than one phase. JP-A-0 1170 675, 0 1182 379, 0 1182 380, 0 1182 381 and 0 1193 376 describe inks which comprise an aqueous phase, in which the dye is dissolved, and an emulsion of oil drops, which contain the UV absorbers and, if desired, also antioxidants. In JP-A-0 1170 673 and 0 1182 382, the oil phase containing UV absorbers is microencapsulated, and the dye is dissolved in the aqueous phase. By contrast, oil-soluble dyes can be dissolved in an oil together with UV absorbers and, if desired, antioxidants. The oil is either emulsified or dispersed in an aqueous phase, as described, for example, in JP-A-0 1170 674 and 0 1170 672. The compounds of the formula (I) are highly suitable for the stabilization of such inks; they are water-soluble and can be dissolved in the aqueous phase.

The novel inks preferably contain 0.01–30% by weight, in particular 0.1–20% by weight, of at least one compound of the formula (I).

Preferred inks contain compounds of the formula (I) as indicated in the description of the preferred compounds.

The compounds can easily be incorporated into inks and recording materials.

The novel recording materials, which are preferably used for the ink-jet printing process and which contain a compound of the formula (I), comprise a support with a surface which can be printed by ink jet. The support is usually paper or a plastic film and is normally coated on one side with a material which is capable of accepting inks. This layer preferably contains $SiO_2$ and polyvinyl alcohol.

Uncoated paper can likewise be employed. In this case, the paper simultaneously serves as support material and ink-accepting layer. It is furthermore possible to use materials comprising cellulose fibres and textile fibre materials, for example cotton fabric or mixed cotton fabric made from cotton and polyacrylamide or polyester, which contain compounds of the formula (I) for ink-jet printing.

The recording materials may also be transparent, as in the case of projection films.

The compounds of the formula (I) can be incorporated into the support material as early as during production thereof, for example by addition to the paper pulp during the production of paper. A second method of application is the spraying of the support material with a solution of the compound of the formula (I). This is an aqueous solution or a solution in a readily volatile organic solvent. The use of emulsions or dispersions is also possible.

Preferably, however, a coating composition with high dye affinity is applied to the support material, and in this case the compounds of the formula (I) are added to this coating composition. The coating compositions generally comprise a solid filler, a binder and conventional additives.

The filler is the major constituent of the coating composition by amount. Examples of suitable fillers are $SiO_2$, kaolin, talc, clay, calcium silicate, magnesium silicate, aluminium silicate, gypsum, zeolite, bentonire, diatomaceous earth, vermiculite, starch or the surface-modified $SiO_2$ described in JP-A-60/260 377. Small amounts of white pigments, for example titanium dioxide, barytes, magnesium oxide, lime, chalk or magnesium carbonate, can be used with the filler in the coating composition if they do not greatly reduce the density of the ink-jet print.

Coating compositions which are intended for transparent, projectable recording materials cannot contain light-scattering particles, such as pigments and fillers.

The binder binds the fillers to one another and to the support material. Examples of customary binders are water-soluble polymers, for example polyvinyl alcohol, partially hydrolysed polyvinyl acetate, cellulose ethers, polyvinylpyrrolidone and copolymers thereof, polyethylene oxide, salts of polyacrylic acid, sodium alginate, oxidized starch, gelatine, casein, vegetable gum, dextrin, albumin, dispersions and polyacrylates or acrylate-methacrylate copolymers, latexes of natural or synthetic rubber, poly(meth)acrylamide, polyvinyl ethers, polyvinyl esters, copolymers of maleic acid, melamin resins, urea resins or chemically modified polyvinyl alcohols, as described in JP-A-61/134 290 and JP-A-61/134 291.

An additional dye receptor or a mordant which improves the fixing of the dye through the coating may be added to the binder. Dye receptors for acidic dyes are of a cationic or amphoteric nature. Examples of cationic receptors are polymeric ammonium compounds, for example polyvinylbenzyltrimethylammonium chloride, polydiallyldimethylammonium chloride, polymethacryloxyethyldimethylhydroxyethylammonium chloride, polyvinylbenzylmethylimidazolium chloride, polyvinylbenzylpicolinium chloride and polyvinylbenzyltributylammonium chloride. Other examples are basic polymers, for example poly(dimethylaminoethyl) methacrylate, polyalkylenepolyamines and condensation products thereof with dicyandiamide, amine-epichlorohydrin polycondensates, or the compounds described in JP-A-57-36 692, 57-64 591, 57-187 289, 57-191 084, 58-177 390, 58-208 357, 59-20 696, 59-33 176, 59-96 987, 59-198 188, 60-49 990, 60-71 796, 60-72 785, 60-161 188, 60-187 582, 60-189 481, 60-189 482, 61-14 979, 61-43 593, 61-57 379, 61-57 380, 61-58 788, 61-61 887, 61-63 477, 61-72 581, 61-95 977, 61-134 291, 62-37 181 or U.S. Pat. No. 4,547,405 and 4,554,181 and DE-A-3 417 582. An example of amphoteric dye receptors is gelatine.

The coating with high dye affinity may contain a number of additives, for example antioxidants, further light stabilizers (including UV absorbers), viscosity improvers, optical brighteners, biocides and/or antistatics.

Examples of suitable antioxidants are, in particular, sterically hindered phenols, hydroquinones and hydroquinone ethers, for example the antioxidants mentioned in GB-A-2 088 777, U.S. Pat. Nos. 5,073,488, 5,089,050 and JP-A-60-72 785, 60-72 786 and 60-71 796.

Examples of suitable light stabilizers are, in particular, organonickel compounds and sterically hindered amines, for example the light stabilizers mentioned in JP-A-58-152 072, 61-146 591, 61-163 886, 60-72 785 and 61-146 591 and GB-A-2 088 777, JP 59-169 883 and 61-177 279.

Suitable UV absorbers which can be added to a coating composition in combination with compounds of the formula (I) are described, for example, in Research Disclosure No. 24239 (1984), page 284, GB-A-2 088 777 and EP-A-0 280 650. Particularly the UV absorbers of the 2-hydroxyphenyl-benzotriazole class and very particularly 2-(2'-hydroxy-3', 5'-di-t-amylphenyl)benzotriazole and 2-(2'-hydroxy-3'-t-butyl-5'-(polyglycol propionate)phenyl)benzotriazole are suitable for use together with compounds of the formula (I) or (II) in recording materials for ink-jet printing. The UV absorbers can be added to the coating composition as emulsions or dispersions.

The coating composition is generally applied to the support, for example paper, and dried by heating. As mentioned above, the compounds of the formula (I) can also be applied to the recording material in a separate operation, alone or together with other components described above, as an aqueous solution. Application can take place by spraying, sizing in a sizing press, a separate pouring operation or by immersion in a trough. After such post-treatment of the recording material, an additional drying operation is necessary.

The recording material preferably contains from 1 to 10000 mg/m², in particular from 50 to 2000 mg/m², of at least one compound of the formula (I).

The present invention furthermore relates to the use of a compound of the formula (I) for stabilizing organic materials and in particular surface coatings against damage by, in particular, radiation (UV light), and to the stabilized organic material or coating itself. Preferred compounds of the formula (I) are mentioned above under the description of the compounds. Examples of compounds of the formula (I) which can be used are described in greater detail under the photographic materials.

The use of the compound of the formula (I) is particularly preferred in surface coatings as described in U.S. Pat. No. 5,106,891 (col. 6, line 55, to col. 7, line 62; incorporated herein by reference). Very particular preference is given to the use of a compound of the formula (I) in automotive paints.

The use of a compound of the formula (I) for stabilizing organic materials and in particular surface coatings can also take place together with sterically hindered amines of the polyalkylpiperidine type. Suitable compounds from the series consisting of derivatives of polyalkylpipefidines contain at least one group of the formula (HA)

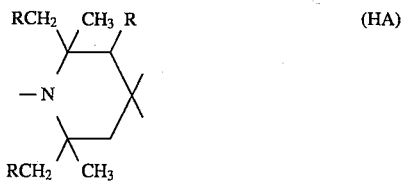

in which R is hydrogen or methyl. Examples of such compounds are given in U.S. Pat. No. 5,106,891 (col. 10, line 1, to col. 27, line 45; incorporated herein by reference). In addition to or instead of the stefically hindered amines, it is advantageous to use a UV absorber from the series consisting of the hydroxyphenylbenzotriazoles, hydroxyphenylbenzophenones, oxanilides or further hyclroxyphenyl-s-triazines with a compound of the formula (I).

The organic materials or surface coatings stabilized according to the invention preferably contain 0.02–5% by weight, particularly preferably 0.05–3% by weight, of a compound of the formula (I), based on the polymer weight (solid).

The present invention furthermore relates to a process for the preparation of the novel compounds of the formula

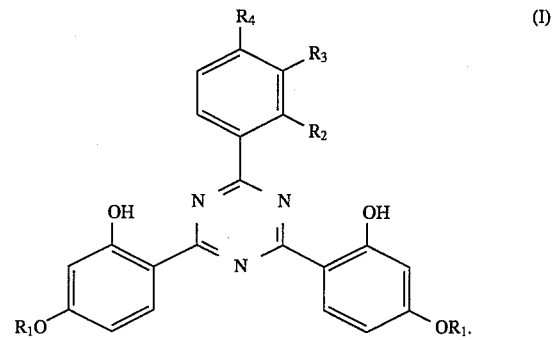

Examples of processes for the preparation of the starting compounds:

aa) Reaction of epichlorohydrin with HO—(CH$_2$CH$_2$O)$_n$—R$_8$ with addition of a base (for example NaOH) to give

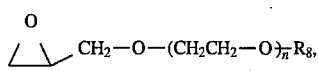

where R$_8$ and n are as defined under the formula (I).

bb) Reaction of HO—(CH$_2$CH$_2$O)$_n$—R$_8$ with COCl$_2$ to give Cl—C(O)O—(CH$_2$CH$_2$O)$_n$—R$_8$ where R$_8$ and n are as defined under the formula (I).

The other starting compounds are known or can be obtained by processes known from the literature.

Examples of processes for the preparation of the compounds of the formula (I):

a1) Reaction of a bisresorcinyltriazine with

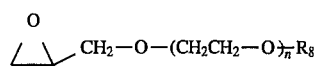

to give

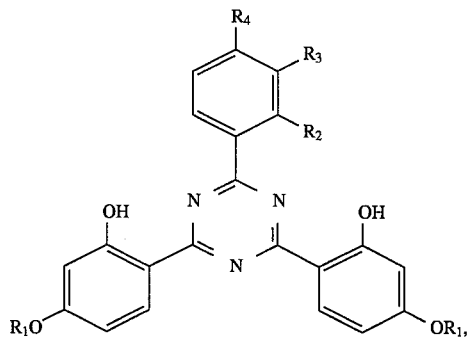

where R$_1$ is CH$_2$—CH(OH)—CH$_2$—O—(CH$_2$CH$_2$—O)$_n$—R$_8$, where R$_2$, R$_3$, R$_4$, R$_8$ and n are as defined under the formula (I).

a2) Reaction of a bisresorcinyltriazine with R$_6$—CH(Br)—C(O)O—R$_{20}$ to give

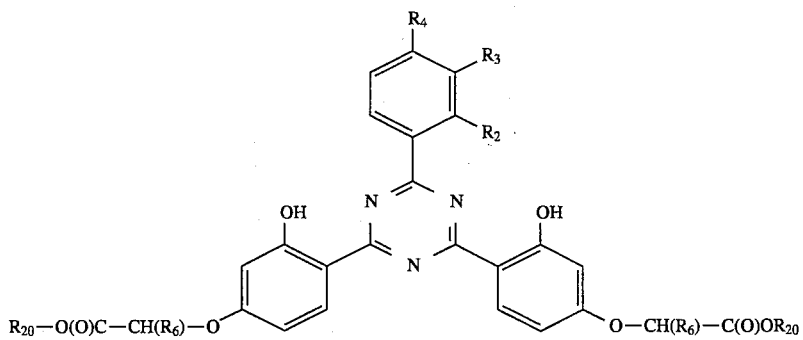

and subsequent esterification thereof by means of HO—(CH$_2$CH$_2$—O)$_n$—R$_8$ to give the novel compound

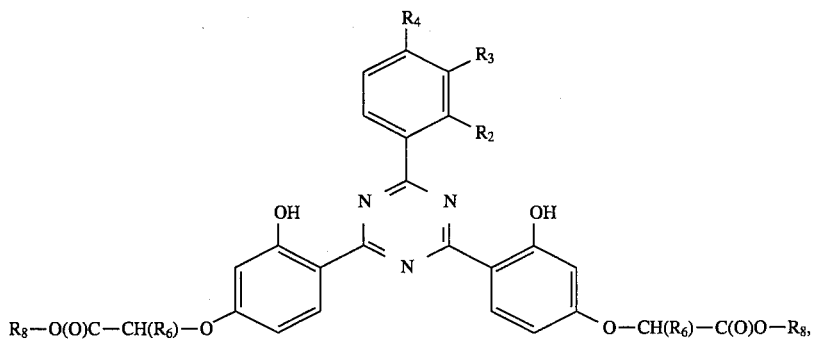

where R$_2$, R$_3$, R$_4$, R$_6$, R$_8$ and n are as defined under the formula (I).

b) Reaction of

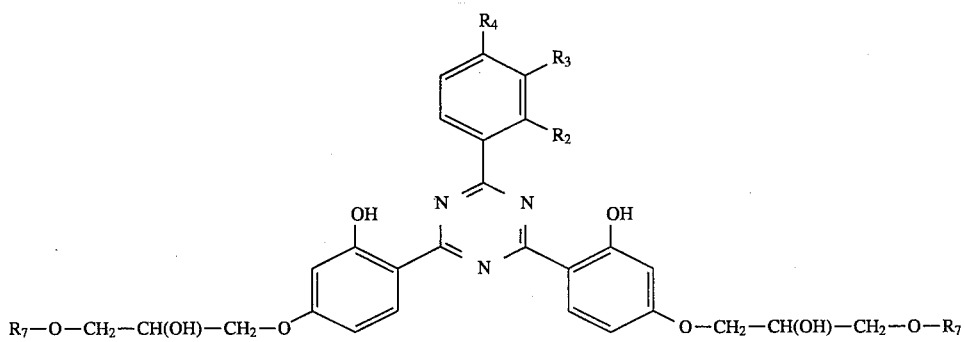

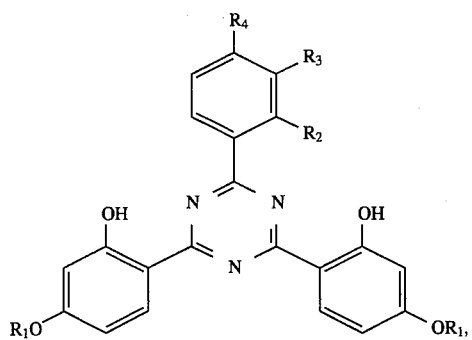

where R$_1$ is CH$_2$—CH(CH$_2$OR$_7$)—O—C(O)—(CH$_2$CH$_2$—O)$_n$—R$_8$ where R$_2$, R$_3$, R$_4$, R$_7$, R$_8$ and n are as defined under the formula (I).

Analogous preparation processes can also be used to give the novel compounds derived from trisresorcinyltriazine.

The examples below illustrate the invention in greater detail, without representing a limitation.

Example 1

Preparation of heptaethylene glycol α-methyl-ω-glycidyl ether 12.0 g (0.30 mol) of sodium hydroxide are dissolved virtually completely in 105.1 g (0.30 mol) of polyethylene glycol (350) monomethyl ether over the course of 3 hours at 80° C. with stirring. The mixture is cooled to 25° C., and 83.2 g (0.90 mol) of epichlorohydrin (Fluka, 99.5%) are added with vigorous stirring, and the temperature of the exothermic reaction is kept below 40° C. by cooling with an ice bath from time to time.

After one hour, the reaction mixture is heated to 75° C., held at this temperature for 2 hours and cooled to 50° C., and the resultant salt (NaCl) is filtered off. The excess epichlorohydrin is removed at 110° C./15 mm and subsequently at 110° C./0.5 mm, giving

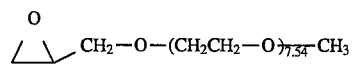

as a slightly viscous, pale yellow liquid.

Example 2

Preparation of 2-phenyl-4,6-bis[2-hydroxy-4-{3'-(methoxyheptaethoxy)2'-hydroxypropoxy}phenyl]-1,3,5-triazine [compound (1)]

A mixture of 10.0 g of 2-phenyl-4,6-bis(2,4-dihydroxy)phenyl)-1,3,5-triazine, 25.8 g of heptaethylene glycol α-methyl-ω-glycidyl ether and 1.10 g of ethyl triphenylphosphonium bromide is kept at 140° C. for 5 hours in 100 ml of mesitylene. The mixture is evaporated on a Rotavapor and transferred onto a silica gel column (Ø=6 cm, h=35 cm; silica gel 60, 230–400 mesh) and eluted with a mixture of methylene chloride/methanol (95/5). Removal of the solvent (110° C./0.01 mm) from the main fraction gives 27.7 g (87.9%) of the compound of the formula

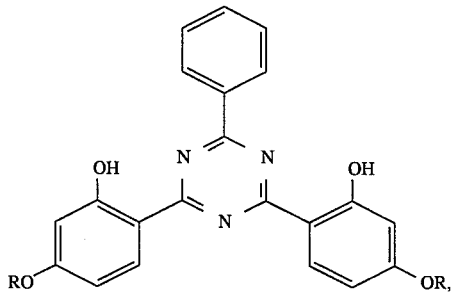

(1)

where R=$CH_2CH(OH)$—$CH_2$—$O(CH_2CH_2O)_{7.54}$—$CH_3$, as a viscous pale yellow oil.

Elemental analysis: $C_{59.2}H_{91.4}N_3O_{23.1}$ Calculated: C58.53; H 7.58; N 3.46% Found: C57.29; H 7.84; N 2.83%

By using the corresponding starting compounds, the compounds listed in Table 2 below can be prepared analogously to the above procedure.

TABLE 2

| Comp. | Formula (MW) | | |
|---|---|---|---|
| (2) | $C_{35}H_{43}N_3O_{10}$ | Calculated | C 63.15; H 6.51; N 6.31% |
|  | (665.75) | Found | C 63.23; H 6.77; N 6.07% |
| (3) | $C_{39}H_{51}N_3O_{10}$ | Calculated | C 64.89; H 7.12; N 5.82% |
|  | (721.86) | Found | C 65.04; H 7.09; N 5.81% |
| (4) | $C_{37}H_{47}N_3O_{12}$ | Calculated | C 61.23; H 6.53; N 5.79% |
|  | (725.80) | Found | C 60.93; H 6.88; N 5.45% |
| (6) | $C_{39}H_{51}N_3O_{12}$ | Calculated | C 62.14; H 6.82; N 5.57% |
|  | (753.85) | Found | C 61.89; H 7.04; N 5.37% |
| (8) | $C_{43}H_{59}N_3O_{12}$ | Calculated | C 63.77; H 7.34; N 5.19% |
|  | (809.96) | Found | C 63.60; H 7.37; N 5.13% |
| (9) | $C_{39}H_{51}N_3O_{13}$ | Calculated | C 60.85; H 6.68; N 5.46% |
|  | (769.85) | Found | C 60.58; H 6.79; N 5.15% |
| (10) | $C_{41}H_{55}N_3O_{14}$ | Calculated | C 60.51; H 6.81; N 5.16% |
|  | (813.90) | Found | C 60.30; H 6.78; N 5.65% |
| (11) | $C_{43}H_{59}N_3O_{14}$ | Calculated | C 61.34; H 7.06; N 4.99% |

TABLE 2-continued

| Comp. | Formula (MW) | | |
|---|---|---|---|
|  | (841.96) | Found | C 60.82; H 7.13; N 4.72% |
| (12) | $C_{47}H_{67}N_3O_{14}$ | Calculated | C 62.86; H 7.52; N 4.68% |
|  | (898.07) | Found | C 63.02; H 7.64; N 4.43% |
| (13) | $C_{77}H_{127}N_3O_{32}$ | Calculated | C 57.56; H 7.97; N 2.62% |
|  | (1606.87) | Found | C 56.87; H 8.25; N 2.33% |
| (15) | $C_{43}H_{55}N_3O_{14}$ | Calculated | C 61.64; H 6.62; N 5.01% |
|  | (837.93) | Found | C 61.35; H 6.69; N 4.99% |
| (16) | $C_{43}H_{55}N_3O_{10}$ | Calculated | C 66.73; H 7.16; N 5.43% |
|  | (773.93) | Found | C 66.67; H 7.20; N 5.24% |
| (17) | $C_{81}H_{135}N_3O_{36}$ | Calculated | C 56.33; H 7.88; N 2.43% |
|  | (1726.97) | Found | C 55.64; H 8.03; N 2.12% |
| (18) | $C_{42}H_{57}N_3O_{15}$ | Calculated | C 59.78; H 6.81; N 4.98% |
|  | (843.93) | Found | C 59.73; H 6.89; N 5.05% |
| (19) | $C_{48}H_{69}N_3O_{15}$ | Calculated | C 62.12; H 7.49; N 4.53% |
|  | (928.10) | Found | C 62.13; H 7.49; N 4.53% |
| (20) | $C_{45}H_{63}N_3O_{18}$ | Calculated | C 57.87; H 6.80; N 4.50% |
|  | (934.01) | Found | C 57.93; H 6.79; N 4.44% |
| (21) | $C_{48}H_{69}N_3O_{18}$ | Calculated | C 59.07; H 7.13; N 4.30% |
|  | (976.09) | Found | C 58.88; H 7.07; N 4.29% |
| (23) | $C_{54}H_{81}N_3O_{18}$ | Calculated | C 61.17; H 7.70; N 3.96% |
|  | (1060.26) | Found | C 60.95; H 7.63; N 4.00% |
| (24) | $C_{48}H_{69}N_3O_{19.5}$ | Calculated | C 57.65; H 6.95; N 4.20% |
|  | (1000.09) | Found | C 57.55; H 6.82; N 4.24% |
| (25) | $C_{51}H_{75}N_3O_{21}$ | Calculated | C 57.45; H 7.09; N 3.94% |
|  | (1066.17) | Found | C 57.17; H 7.16; N 3.75% |
| (26) | $C_{60}H_{93}N_3O_{21}$ | Calculated | C 60.44; H 7.86; N 3.52% |
|  | (1192.42) | Found | C 60.38; H 7.87; N 3.62% |
| (27) | $C_{105}H_{183}N_3O_{48}$ | Calculated | C 55.91; H 8.18; N 1.86% |
|  | (2255.62) | Found | C 54.84; H 8.38; N 1.37% |
| (28) | $C_{45}H_{57}N_3O_{18}$ | Calculated | C 58.25; H 6.19; N 4.53% |
|  | (927.97) | Found | C 58.13; H 6.21; N 4.33% |
| (29) | $C_{51}H_{69}N_3O_{21}$ | Calculated | C 57.78; H 6.56; N 3.96% |
|  | (1060.12) | Found | C 57.49; H 6.84; N 3.28% |

Example 3

The novel UV absorbers are incorporated with stirring into a water-borne varnish of the following composition:

| | |
|---|---|
| Bayhydrol ® VP LS 2986 E (45%)[1] | 72.0 |
| Cymel ® 327 (90%)[2] | 15.4 |
| Butyl diglycol | 10.44 |
| Fluorad ® FC 170 (100% in water)[3] | 0.72 |
| Lanco-Thix PUR 21[4] | 0.72 |
| Byk 301[5] | 0.72 |
| | 100.0 |

[1] Acrylate resin (Bayer, D)
[2] Melamine resin (American Cyanamid, USA)
[3] Wetting agent (3M, D)
[4] Thickener (Langer & Co., D)
[5] Flow-control agent (Byk-Chemie, D)

The vanish prepared in this way is thinned with water to a spraying consistency and applied to a prepared substrate (coil-coated aluminium sheet, automotive filler, water-borne silver-metallic base coat).

The coating is dried for about 20 minutes at room temperature, and for 20 minutes at 70° C. and then baked for 20 minutes at 140° C., giving a dry film thickness of about 35–40 μm.

The comparison used is a varnish produced in the same way but containing no UV absorber.

The samples are weathered in a Xenon-weatherometer® unit (Atlas Corp.) (cycle: CAM 180)

The gloss (DIN 67530) and cracking (TNO scale) are measured.

TABLE 3

| stabilization* | 20° gloss after ... hours | | | |
|---|---|---|---|---|
| | 0 | 400 | 800 | 1200 |
| unstabilized | 90 | 33 | 28 | 10 |
| 1.5% of compound (4) | 92 | 88 | 83 | 76 |
| 1.5% of compound (11) | 88 | 82 | 77 | 72 |
| 1.5% of compound (12) | 92 | 88 | 83 | 76 |
| 1.5% of compound (21) | 92 | 90 | 88 | 83 |
| 1.5% of compound (25) | 91 | 85 | 78 | 73 |
| 1.5% of compound (26) | 86 | 82 | 73 | 70 |

*% based on the solids content

The stabilized formulations exhibit better gloss retention and less cracking than the comparison example which shows cracking after 1200 hours.

Example 4

The novel UV absorbers are pre-dissolved in about 5–10 g of xylene and incorporated into a varnish of the following composition:

| | |
|---|---|
| Uracron ® 2263 XB (50%)[1)] | 54.5 |
| Cymel ® 327 (90%)[2)] | 16.3 |
| Butyl glycol acetate | 5.5 |
| Xylene | 19.4 |
| n-Butanol | 3.3 |
| Baysilon ® A (1% in xylene)[3)] | 1 |
| | 100.0 |

[1)]Acrylate resin (DSM, NL)
[2)]Melamine resin (American Cyanamid, USA)
[3)]Flow-control agent (Bayer, D)

The varnish prepared in this way is thinned to a spraying consistency using butyl glycol acetate/n-butanol/xylene (1/6/13) and applied to a prepared substrate (coil-coated aluminium sheet, automotive filler, silver-metallic base coat). After a drying time of about 15 minutes, the coating is baked at 130° C. for 30 minutes, giving a dry film thickness of about 40–45 μm.

The comparison used is a varnish produced in the same way but containing no UV absorber.

The samples are weathered in a UVCON® unit (Atlas Corp.) (UVB-313 lamps; cycle: 8 h UV, 70° C.; 4 h cond., 50° C.).

The 20° gloss (DIN 67530) is measured. The stabilized samples exhibit better gloss retention than the unstabilized comparison sample.

The results are shown in Table 4.

TABLE 4

| Stabilization* | 20° gloss after ... hours UVCON ® | | | | |
|---|---|---|---|---|---|
| | 0 | 800 | 1200 | 1600 | 2000 |
| Unstabilized | 87 | 55 | 15 | | |
| 1.5% of compound (1) | 88 | 74 | 80 | 79 | 51 |
| 1.5% of compound (17) | 87 | 71 | 73 | 52 | 39 |
| 1.5% of compound (1) 0.7% of Tinuvin 292** | 87 | 84 | 84 | 85 | 83 |
| 1.5% of compound (17) 0.7% of Tinuvin 292 | 87 | 83 | 79 | 83 | 82 |

*% based on the solids content of the varnish
**sterically hindered amine (Ciba-Geigy, CH)

Example 5

Gelatine layers of the following composition (per m$^2$) are applied to a polyester support:

| Component | Amount |
|---|---|
| Gelatine | 1200 mg |
| Hardening material | 40 mg |
| Dispersant | 100 mg |
| Compound of the formula (I) | 400 mg |

The hardening material is 2-hydroxy-4,6-dichloro-1,3,5-triazine.

The dispersant is sodium-4,8-diisobutyl-naphthalene-2-sulfonate.

The prepared coatings are dried and hardened at 20° C. for 7 days.

When compounds (1), (15) or (17) are used, clear transparent photographic layers are obtained.

Example 6

Preparation of 2-phenyl-4,6-bis[2-hydroxy-4-{(methoxytriethoxycarbonyl)-2-ethoxy}phenyl]1,3,5-triazine [Compound (14)]

A mixture of 10.0 g (17 mmol) of 2-phenyl-4,6-bis[2-hydroxy-4-(ethoxycarbonyl)2-ethoxy)phenyl]-1,3,5-triazine, 18.1 g (110 mmol) triethylene glycol monomethyl ether and 0.4 g (1.6 mmol) of dibutyltin oxide are kept at 120 ° C. for 16 hours, during which ethanol is removed using a Hickmann condenser. The mixture is evaporated on a Rotavapor and transferred to a silica gel column (∅=6 cm, h=35 cm; silica gel 60, 230–400 mesh) and eluted with ethyl acetate. Removal of the solvent (150° C./0.1 mm)from the main fraction gives 11.8 g (84% yield)of the compound of formula

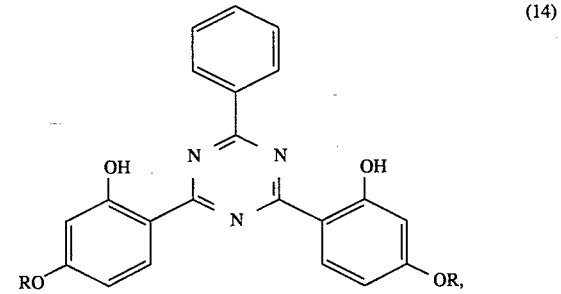

(14)

where R=CH(CH$_3$)—C(O)O—(CH$_2$CH$_2$O)$_3$—CH$_3$, as a viscous, pale yellow oil.

Elemental analysis :C$_{41}$H$_{51}$N$_3$O$_{14}$ Calculated: C60.81; H6.35; N5.19% Found: C60.75; H6.36; N5.03%

What is claimed is:

1. A compound of the formula

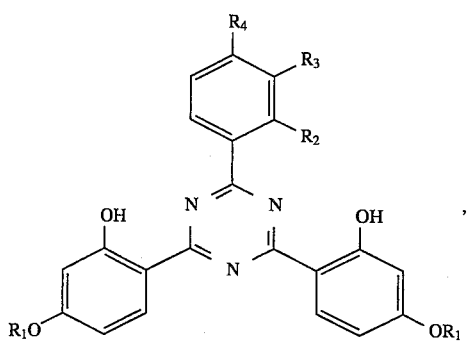

in which the radicals

R₁, independently of one another, are $-(CH_2CHR_5-O)_k-R_8$, $-CH_2-CH(OH)-CH_2-O-(CH_2CHR_5-O)_n-R_8$, $-(CH_2)_l-CHR_6-C(O)-O-(CH_2CHR_5-O)_n-R_8$ or $-CH_2-CH(CH_2-OR_7)-O-C(O)-(CH_2CHR_5-O)_n-R_8$;

R₂ is H, OH, $C_1-C_{12}$alkyl, F or Cl;

R₃ is H, OR₉, $C_1-C_{12}$alkyl, F or Cl;

R₄ is H, OR₉, $C_1-C_{12}$alkyl, F, Cl or, if R₂ is OH, is alternatively OR₁;

R₅ is H or CH₃;

R₆ is $C_1-C_{16}$alkyl or, if l is not 1, is alternatively H;

R₇ is $C_1-C_{14}$alkyl or phenyl;

R₈ is H, $C_1-C_{14}$alkyl, phenyl or $C_1-C_4$alkylphenyl;

R₉ is $C_1-C_4$alkyl;

k is a number from 2 to 16;

l is a number from 0 to 16 and n is a number from 1 to 16.

2. A compound according to claim 1, wherein, in the formula (I), the radicals R₁, independently of one another, are $-(CH_2CHR_5-O)_k-R_8$, $-CH_2-CH(OH)-CH_2-O-(CH_2CHR_5-O)_n-R_8$, $-(CH_2)_l-CHR_6-C(O)-O-(CH_2CHR_5-O)_n-R_8$ or $-CH_2-CH(CH_2-OR_7)-O-C(O)-(CH_2CHR_5-O)_n-R_8$;

R₂ is H, OH, $C_1-C_8$alkyl, F or Cl;

R₃ is H, OR₉, $C_1-C_8$alkyl, F or Cl;

R₄ is H, OR₉, $C_1-C_8$alkyl, F, Cl or, if R₂ is OH, is alternatively OR₁;

R₅ is H;

R₆ is $C_1-C_{12}$alkyl or, if l is not 1, is alternatively H;

R₇ is $C_1-C_8$alkyl;

R₈ is H or $C_1-C_{10}$alkyl;

R₉ is $C_1-C_4$alkyl;

k is a number from 2 to 12;

l is a number from 0 to 12, and n is a number from 1 to 12.

3. A compound according to claim 1, wherein, in the formula (I), the radicals R₁, independently of one another, are $-CH_2-CH(OH)-CH_2-O-(CH_2CHR_5-O)_n-R_8$ or $-(CH_2)_l-CHR_6-C(O)-O-(CH_2CHR_5-O)_n-R_8$;

R₂ is H, OH or $C_1-C_4$alkyl;

R₃ is H, OR₉ or $C_1-C_4$alkyl;

R₄ is H, OR₉, $C_1-C_4$alkyl, F, Cl or, if R₂ is OH, is alternatively OR₁;

R₅ is H;

R₆ is $C_1-C_6$alkyl;

R₈ is $C_1-C_4$alkyl;

R₉ is $C_1-C_4$alkyl;

l is 0, and n is a number from 1 to 12.

\* \* \* \* \*